US00RE50048E

(19) United States
(12) Reissued Patent
Kercher et al.

(10) Patent Number: US RE50,048 E
(45) **Date of Reissued Patent: *Jul. 23, 2024**

(54) FLUID-POWERED ELONGATION INSTRUMENTATION FOR CORRECTING ORTHOPEDIC DEFORMITIES

(71) Applicant: University of Utah Research Foundation, Salt Lake City, UT (US)

(72) Inventors: James Kercher, Atlanta, GA (US); John Helfin, Atlanta, GA (US)

(73) Assignee: University of Utah Research Foundation, Salt Lake City, UT (US)

( * ) Notice: This patent is subject to a terminal disclaimer.

(21) Appl. No.: 16/998,339

(22) Filed: Aug. 20, 2020

Related U.S. Patent Documents

Reissue of:
(64) Patent No.: 10,052,134
Issued: Aug. 21, 2018
Appl. No.: 14/727,460
Filed: Jun. 1, 2015

U.S. Applications:
(63) Continuation of application No. 12/474,109, filed on May 28, 2009, now Pat. No. 9,060,810.
(Continued)

(51) Int. Cl.
*A61B 17/70* (2006.01)
*A61B 17/00* (2006.01)

(52) U.S. Cl.
CPC ..... *A61B 17/7017* (2013.01); *A61B 17/7011* (2013.01); *A61B 17/7014* (2013.01); *A61B 17/7016* (2013.01)

(58) Field of Classification Search
CPC ..... A61B 17/7017; A61B 17/7011; A61B 17/7014; A61B 17/7016
See application file for complete search history.

(56) References Cited

U.S. PATENT DOCUMENTS 3,916,950 A 11/1975 Mongerson et al.
4,212,087 A 7/1980 Mortensen
(Continued)

OTHER PUBLICATIONS

Masashi Takaso, et al., "New remote-controlled growing-rod spinal instrumentation possibly applicable for scoliosis in young children", believed to have been published May 28, 2008,5 pages, Journal of Orthopaedic Science—The Japanese Orthopaedic Assoc.
(Continued)

*Primary Examiner* — Beverly M Flanagan
(74) *Attorney, Agent, or Firm* — WORKMAN NYDEGGER

(57) ABSTRACT

Growing rod systems and methods for correcting spinal deformities include at least one growing rod assembly and at least one fluid delivery assembly. Each growing rod assembly includes a fluid actuator that is operable to extend first and second rod segments in opposite directions along the spine. The fluid actuator can be provided by, for example, a piston-cylinder actuator. Each fluid delivery assembly includes a fluid pump operably connectable to a fluid line, which in turn is connected to the fluid actuator. In one embodiment, the fluid actuator is of a linear design. In another embodiment, two linear or curvilinear fluid actuators are provided back-to-back and connected by a connecting rod that mounts to the mid-spine and is contourable. In another embodiment, the fluid actuator is of a curvilinear design to generally conform the normal spine. And in another embodiment, the fluid actuator includes a fluid-over-fluid shock absorber.

37 Claims, 16 Drawing Sheets

Related U.S. Application Data

(60) Provisional application No. 61/056,654, filed on May 28, 2008.

(56) References Cited

U.S. PATENT DOCUMENTS

| | | | | |
|---|---|---|---|---|
| 5,350,379 | A | 9/1994 | Spievack | |
| 5,466,261 | A | 11/1995 | Richelsoph | |
| 5,516,122 | A | 5/1996 | Caffee | |
| 5,672,175 | A | 9/1997 | Martin | |
| 5,720,746 | A | 2/1998 | Soubeiran | |
| 6,106,525 | A | 8/2000 | Sachse | |
| 6,364,883 | B1 | 4/2002 | Santilli | |
| 6,520,991 | B2 | 2/2003 | Huene | |
| 6,554,831 | B1 | 4/2003 | Rivard et al. | |
| 6,835,207 | B2 | 12/2004 | Zacouto et al. | |
| 7,052,498 | B2 | 5/2006 | Levy et al. | |
| 7,326,248 | B2 | 2/2008 | Michelson | |
| 7,465,317 | B2 | 12/2008 | Malberg et al. | |
| 2001/0029375 | A1 | 10/2001 | Betz et al. | |
| 2006/0009767 | A1 | 1/2006 | Kiester | |
| 2006/0264914 | A1* | 11/2006 | Furst | A61F 2/91 606/1 |
| 2007/0191846 | A1 | 8/2007 | Bruneau et al. | |
| 2008/0147194 | A1 | 6/2008 | Grotz et al. | |
| 2008/0161933 | A1 | 7/2008 | Grotz et al. | |
| 2009/0112207 | A1 | 4/2009 | Walker et al. | |
| 2009/0306717 | A1* | 12/2009 | Kercher | A61B 17/7011 606/258 |

OTHER PUBLICATIONS

Alberto M. Pernia, et al., "Children's anti-scoliotic fixators with transcutaneous electronic activation", 2008, 29 pages, www.elsevier.com.

* cited by examiner 116a
110
120
112
118
122
160
114
164
116b
168

116a 134
140
138
120
138

134
136
142
144
146
112
132
118

124
122
138
126
116a
160
162
116b

FLUID-POWERED ELONGATION INSTRUMENTATION FOR CORRECTING ORTHOPEDIC DEFORMITIES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application is a continuation of a U.S. Non-Provisional patent application Ser. No. 12/474,109, filed May 28, 2009, which claims the priority benefit of U.S. Provisional Patent Application Ser. No. 61/056,654, filed May 28, 2008, all of which are hereby incorporated herein by reference.

TECHNICAL FIELD

The present invention relates generally to surgical instrumentation and methods for correcting spinal deformities and, more particularly, to spinal growing-rod surgical instrumentation and methods.

BACKGROUND

Scoliosis is a medical condition in which a person's spine is abnormally curved and/or rotated. It is typically classified as congenital (caused by anomalies at birth), neurologic (occurring secondary to central nervous system disorders), or idiopathic (developing over time without definite cause). Idiopathic scoliosis is further sub-classified according to the age at which it occurs, earlier onset being associated with worse prognosis. Treatment of children with progressive scoliosis occurring at a young age is a difficult problem. Left untreated, progressive curves can produce significant deformity leading to deleterious effects on the developing heart and lungs resulting in a shortened lifespan.

Standard treatment for scoliosis includes spinal fusion surgery. This has limited use in younger children because of the potential alteration or cessation of spinal growth, which in turn can have adverse effects on axial growth, chest wall development, and lung development.

There are known methods to treat spinal deformities in the developing child that avoid spinal fusion. These include external bracing and surgery without spinal fusion. However, most early onset scoliosis is rapidly progressive and largely resistant to bracing, and compliance with brace-wearing regimens is generally very poor, which often makes surgical correction the preferred option.

Known non-fusion, growth-preserving surgical procedures include the placement of special spinal instrumentation known as growing rods. Growing rods are devices placed surgically within a patient's back that provide internal bracing in an effort to limit curve progression. An example of a prior art growing rod system 10 is shown in FIGS. 1-3. The system 10 includes dual, parallel growing rods 12 that are secured to vertebrae of a spine 14 above and below the deformity, thus spanning the curve being addressed. The growing rods 12 are secured to the spine 14 at foundation sites 16 by mounting hardware 18 (e.g., including mounting clamps, screws, and/or hooks) to form fixation constructs. Typically, two rods 12 are implanted in a parallel arrangement with one on each lateral side of the spine 14. Each rod 12 is typically composed of two independent rod segments that are longitudinally coupled together using tandem connectors 20. This configuration allows the rods 12 to be longitudinally adjusted (e.g., telescopically) at regular intervals to provide an overall increase in length.

Growing rod placement is an accepted technique that allows correction of deformity without preventing normal axial growth of the spine. This method requires frequent periodic lengthening of the rod system to adjust for longitudinal growth of the spine as the patient matures. Lengthening is performed by loosening the connectors, using a distraction device to push the rod segments apart until the appropriate amount of lengthening has been achieved, and retightening the connectors.

A fundamental strength of this existing growing-rod design over earlier treatments is also a significant weakness. Beneficially, serial lengthening allows the spine to grow. However, it also requires frequent returns to the operating room. Patients treated with this technique typically need repeat surgeries as frequently as every four to six months. This places the child at significantly increased risk for bleeding, infection, wound, and pulmonary complications. Additionally, overnight observation in a hospital is often necessary. Furthermore, young children with severe spinal deformities often have multiple other medical issues resulting in an overall compromised health status, and stress from repeated surgery can be overly burdensome on these patients and their families.

A second issue with current growing rod techniques relates to the timing of the expansion. Growing rods are generally left in place for a period of months before the patient is taken back to the operating room for lengthening. These interval periods allow the tissues surrounding the rods to heal, but also to scar. Scarred tissue within the telescoping connector parts is difficult and time-consuming to dissect, is more prone to infection, and complicates rod expansion. Scar tissue may also serve to further tether the growing spine, thus adding an additional deforming force. In addition, despite periodic lengthening, the interval placement of instrumentation can frequently result in cessation of spinal growth, which ultimately leads to premature fusion of the immature spine.

A third issue with current growing rod techniques relates to the expansion being only linear. When viewed from the side (the sagittal plane), the normal spine is a compound curve consisting of a lumbar curvature that is defined as lordotic or concave with respect to the ventral (front) surface of the body, a thoracic curve that is defined as kyphotic or convex with respect to the ventral surface of the body, and a cervical curve that is lordotic. The degree of curvature defines one's posture and the "sagittal balance," which is the position of the head over the pelvis when viewed from the side.

All of the known growing-rod devices attempt to control curvature of the spine in a growing child using linear expansion. That is, as the spine elongates, the rods can be extended only linearly. Although the rods themselves can be bent and contoured somewhat (see FIG. 3), the expansion coupling is linear, so when the growing rod system is expanded the rods are moved only linearly. While this does provide some control of curvature in the coronal plane (front-to-back), this does not account for the natural curvature of the spine in the sagittal plane. Accordingly, when using known linear growing-rod systems, either spinal growth and alignment must be altered from their preferred normal curved state, or the fixation constructs (or another component of the growing-rod system) will fail.

If the rods and fixation constructs are strong enough to avoid failure, the spine will be forced to grow in a linear direction. This results in what is known as hypokyphosis or "acquired flatback deformity" of the thoracic spine. This affects the patient's overall sagittal balance and can result in what is known as negative sagittal balance in which the patient's head is centered posterior to its normal position thus negatively affecting overall posture, which results in chronic thoracic and lumbar pain. Even more potentially problematic for the patient is the possibility of junctional kyphosis. This occurs when the spine abnormally "kinks" at the end of the fixation constructs. With severe sagittal imbalance and hypokyphosis, it is thought that junctional kyphosis is much more likely to occur. This can result in catastrophic neurologic injury to the patient when severe and typically results in revision surgery.

If the fixation constructs are not strong enough or if the bone quality is poor, there is potential for construct failure or pullout from the bony foundation sites due to excessive stress on the system. This typically occurs at the more superior foundation sites on the thoracic spine. In the best case scenario, construct failure results in loss of spinal correction and revision surgery is thus required. In the worst case, the metal screws or hooks can pull out of bone and cause direct injury to the spinal cord resulting in paralysis or theoretically even death, the former having been reported in the medical literature.

Accordingly, it can be seen that a need exists for improved surgical instrumentation and methods for bone-deformity correction. It is to the provision of solutions meeting this need that the present invention is primarily directed.

SUMMARY

Generally described, the present invention relates to devices and methods for correcting and/or maintaining otherwise progressive orthopedic deformities in the spine and/or long bones in humans and/or other animals while also preserving normal anatomic bony growth. In the embodiments described herein, there are provided growing rod systems that include at least one growing rod assembly and at least one fluid delivery assembly. Each growing rod assembly includes a fluid actuator that is operable to extend first and second rod segments in opposite directions along the spine. The fluid actuator can be provided by, for example, a piston-cylinder actuator. Each fluid delivery assembly includes a fluid pump operably connectable to a fluid line, which in turn is connected to the fluid actuator.

In a first example embodiment, the fluid actuator is of a linear piston-cylinder design, with the first rod segment extending longitudinally from the piston and the second rod segment extending longitudinally from the cylinder. In a second example embodiment, first and second piston-cylinder actuators are provided, with the first rod segment extending longitudinally from the first piston, the second rod segment extending longitudinally from the second piston in the opposite direction, and the two cylinders connected by a connecting rod that can be countered and mounted to the mid-spine. In a third example embodiment, the fluid actuator is of a curvilinear design, with the piston and the cylinder having a constant radius of curvature that generally conforms to that of the normal spine. And in a fourth example embodiment, the fluid actuator includes a gas-over-fluid shock absorber that dissipates impacts on the spine and helps to prevent pre-mature or unwanted intervertebral fusion.

The specific techniques and structures employed by the invention to improve over the drawbacks of the prior devices and accomplish the advantages described herein will become apparent from the following detailed description of the example embodiments of the invention and the appended drawings and claims.

DESCRIPTION OF EXAMPLE EMBODIMENTS

Figure 1:
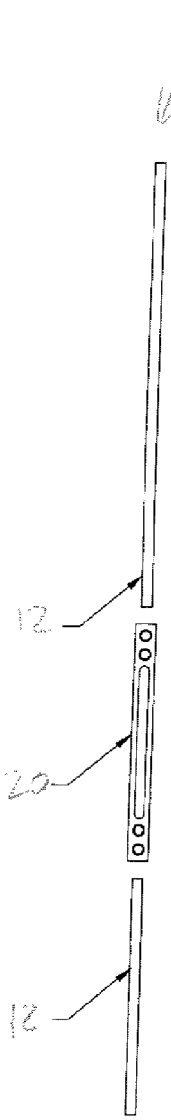
FIG. 1 PRIOR ART
FIG. 1 is a rear view of a prior art growing rod system.
Figure 2:
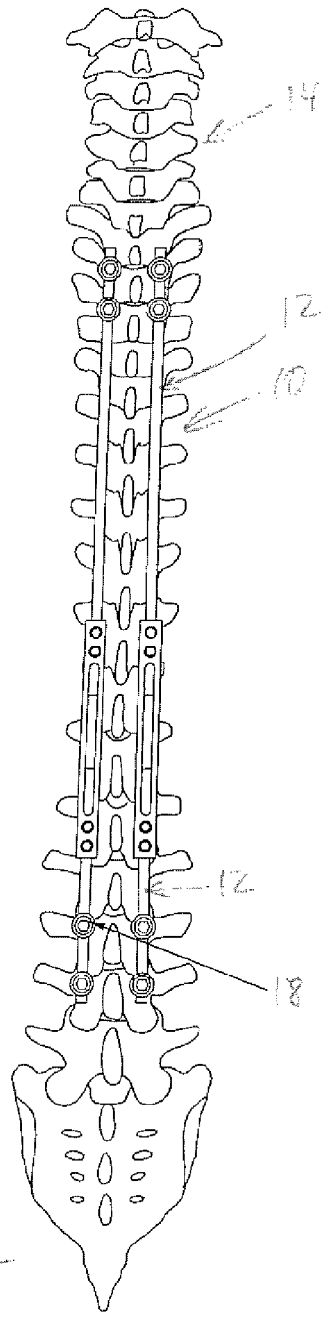
FIG. 2 PRIOR ART
FIG. 2 shows the prior art growing rod system of FIG. 1 in use mounted on a spine.
Figure 3:
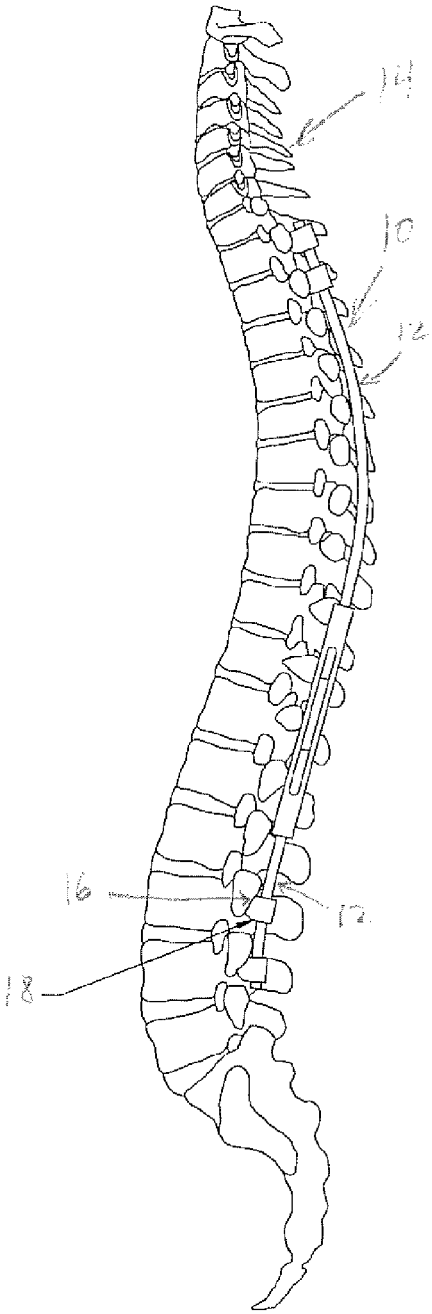
FIG. 3 PRIOR ART
FIG. 3 is a left side view of the prior art growing rod system and spine of FIG. 2.

Referring to the drawings, FIGS. 4-10 show a fluid-powered elongation instrumentation (growing rod) system 110 according to a first example embodiment. The system 110 includes at least one growing rod assembly 112 and at least one fluid supply assembly 114. In the depicted embodiment, the system 110 includes two growing rod assemblies 112 and two fluid supply assemblies 114 (see FIGS. 9 and 10), though one, three, or another number of these could be used in a given application.

The system 110 uses an actuating fluid (i.e., a liquid or gas), delivered by the fluid supply assemblies 114, to expand the growing rod assemblies 112. In typical commercial embodiments, the actuating fluid is a hydraulic fluid such as mineral oil, glycerin, silicon oil, or some other biocompatible viscous substance. In alternative embodiments, the actuating fluid is a compressed gas such as nitrogen or compressed air. The actuating fluid does not have to have the same thermal and flow properties of standard hydraulic fluid, as the volume flow rate through the system 110 is relatively slow such that it is not subject to rapid heating and cooling or to turbulent flow.

Figure 4:
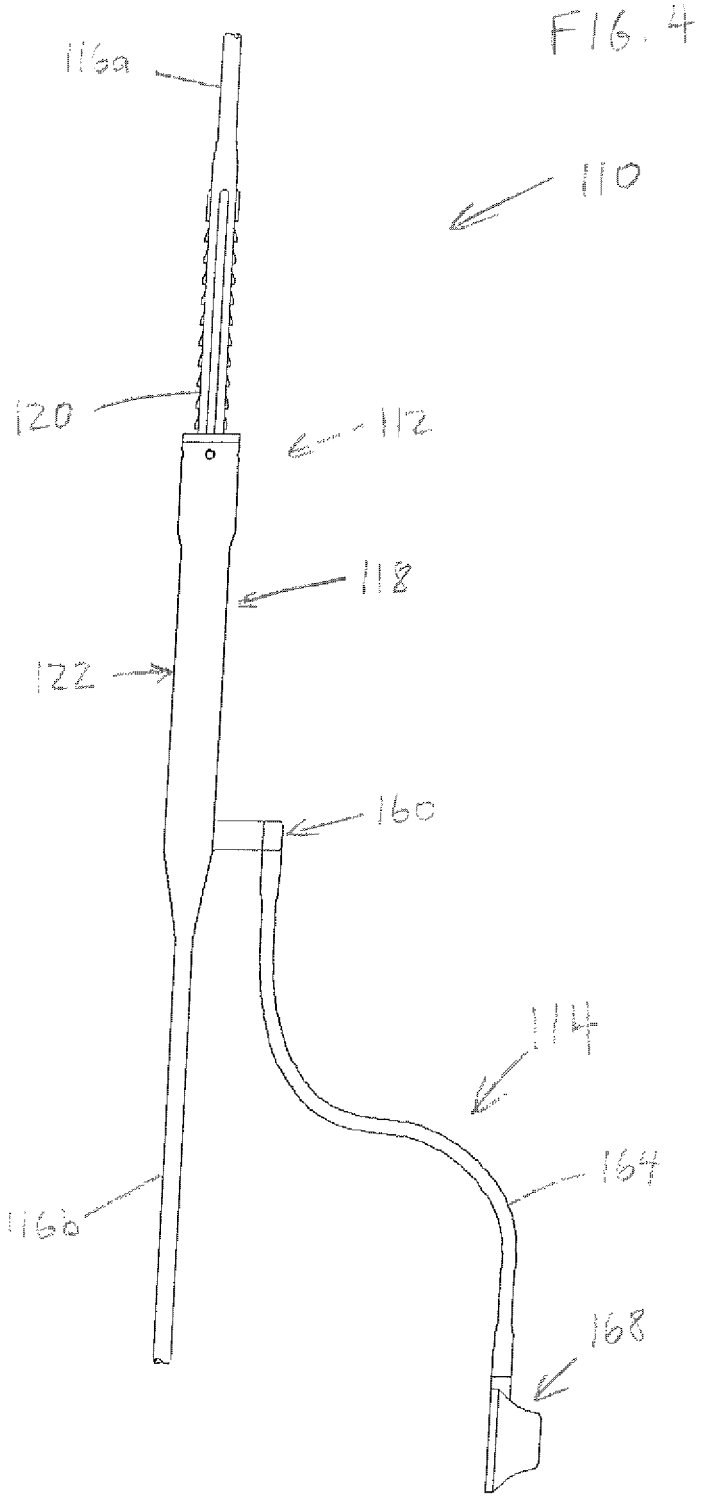
FIG. 4 is a rear view of a growing rod system according to a first example embodiment of the present invention, showing a growing rod assembly and a fluid delivery assembly.
Figures 5, 6, 7:
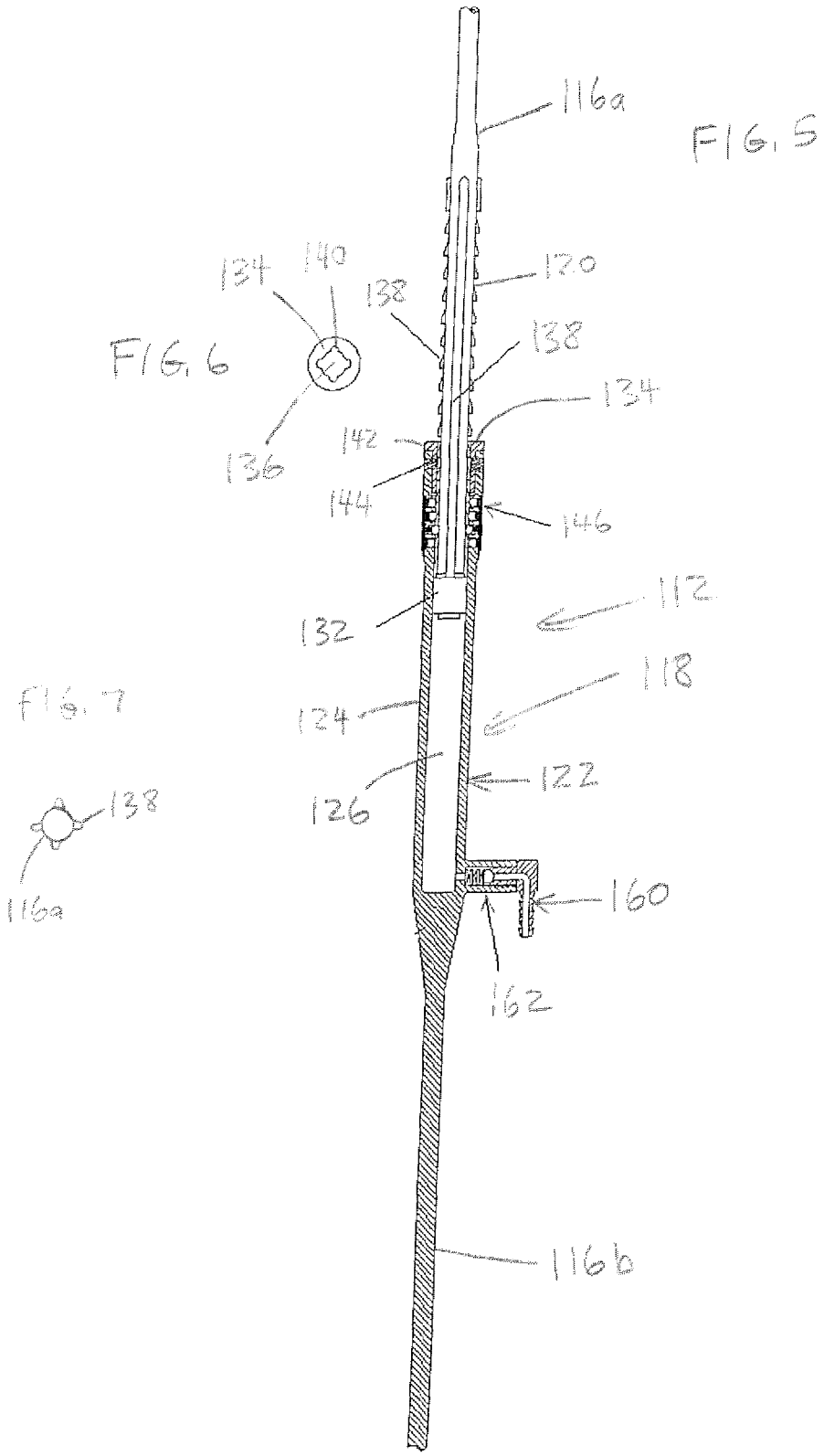
FIG. 5 is a longitudinal cross-section view of the growing rod assembly of FIG. 4, showing details of a piston-cylinder actuator.
FIG. 6 is an end view of an endcap of the cylinder of the growing rod assembly of FIG. 5.
FIG. 7 is an end view of the piston of the growing rod assembly of FIG. 5.

Referring to FIGS. 4 and 5, the growing rod assemblies 112 each include a first rod segment 116a and a second rod segment 116b (collectively, the "rod segments 116"), as well as at least one fluid actuator 118 configured longitudinally between them. The fluid actuator 118 is operable to extend the rod segments 116 in opposite directions (i.e., to extend one of the rod segments relative to the other), thereby providing the desired longitudinal expansion. The fluid actuator 118 can be provided by, for example, the depicted piston-cylinder actuator. In alternative embodiments, the actuator can be of a non-fluid type such as a ratchet-pawl system, a magnetically indexed system, an electric motor and gearing, a solenoid, or the like. The piston-cylinder actuator 118 includes a piston 120 and a cylinder 122 that reciprocate relative to each other. The cylinder 122 includes a peripheral cylinder wall 124 that defines an internal bore 126 within which the piston 120 is reciprocatingly received. The piston 120 telescopes in a linear fashion relative to the internal bore 126 of the hollow cylinder 122. The first rod segment 116a extends longitudinally from the piston 120 and the second rod segment 116b extends longitudinally from the cylinder 122 (or vice versa).

The rod segments 116 are affixed to the patient's spine 130 in a conventional fashion using commercially available mounting hardware 128. That is, one of the rod segments 116 is affixed to the spine 130 at a foundation site selected to be above the deformity and the other one of the rod segments is affixed to the spine at a foundation site selected to be below the deformity. The mounting hardware 128 can be provided by for example pedicle screws, lamina hooks, pedicle hooks, or other known mounting devices. These known mounting hardware elements have a proven track record of successful instrumentation fixation on the spine.

The first rod segment 116a and the piston 120 can be integrally fabricated together as a single piece or they can be fabricated separately and attached together using conventional manufacturing/assembly techniques. Similarly, the second rod segment 116b and the cylinder 122 can be integrally fabricated together as a single piece or they can be fabricated separately and attached together using conventional manufacturing/assembly techniques. For example, the rod segments 116 and their respective piston-cylinder components 120 and 122 can be separately formed and attached together using end-to-end rod connectors available in current spinal-elongation instrumentation sets or using slotted, detent, or threaded connections. In any case, the rod segments 116 are effectively continuations/extensions of the piston 120 and the cylinder 122.

The rod segments 116 can be sized and shaped similarly to conventional growing rods. In a typical commercial embodiment, for example, the rod segments 116 are cylindrical and have diameters of about 4.5 mm to about 6.35 mm. In this way, existing mounting hardware 128 can be used to mount the rod segments 116 to the spine 130 (see FIGS. 9 and 10). In alternative embodiments, the rod segments can have a rectangular, polygonal, or other regular or irregular cross-sectional shape and/or can have other diameters (or other lateral "thickness" dimensions for non-cylindrical rod segments) selected for providing the desired strength and rigidity. In addition, the rod segments 116 and the fluid actuator 118 can have a combined length (in a retracted position and an extended position) that is similar to that of conventional growing rods used in spinal instrumentation.

The rod segments 116 can be made of a material with a sufficient shear modulus and fatigue strength to permit slight cyclic deflections without failure. In addition, the material selected to make the rod segments 116 can be sufficiently ductile to permit the rods segments to be plastically deformed into a curve (i.e., contoured) to generally conform to the natural curvature of the spine 130 and also sufficiently strong to aid in correction of the spinal deformity. Contouring of the rod segments 116 can be done using currently available rod contouring tools and techniques. Suitable materials for making the rod segments 116 include, for example, surgical stainless steels, nickel chromium alloys, titanium alloys, or polyetheretherketone (PEEK) or other high-strength thermoplastics. When making the rod segments 116 of a rigid material with a low ductility that does not readily permit custom contouring the rod segments to the individual patient's spine by the surgical or prep team, the rod segments can be provided in pre-set anatomic contours based for example on the average or ideal spinal curve for young people.

The cylinder 120 and the piston 122 can be made of the same material as the rod segments 116 or they can be made of a different material that is selected for high strength and rigidity and for withstanding the system operating pressure. In a typical commercial embodiment, the growing rod assembly 112 is designed for withstanding operating pressures of from about 0.0 psi up to about 1,000 psi, with a factor of safety of about at least 5. Suitable materials for making the cylinder wall 124 and the piston 120 include, for example, stainless steels, nickel chromium alloys, titanium alloys, or PEEK or other high-strength thermoplastics or other known materials that are used to construct conventional piston-cylinder actuators. Using such a material, the cylinder wall 124 can have a thickness of for example about 1.0 mm to about 2.0 mm and form the internal bore with a diameter of for example about 6.0 mm to about 8.0 mm, thereby allowing a pushing force of about 195 Newtons to about 340 Newtons at about 1,000 psi. In alternative embodiments, the piston, the cylinder wall, and the cylinder bore can have other diameters or other thicknesses selected for providing the desired strength and rigidity and for withstanding an alternative operating pressure.

Figure 11:
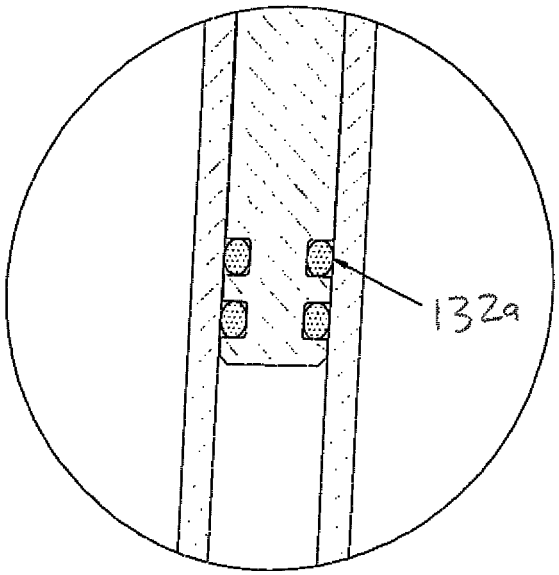
FIG. 11 is a detail view of a portion of piston-cylinder actuator of a growing rod assembly according to an alternative embodiment, showing details of an alternative sealing system.
Figure 13:
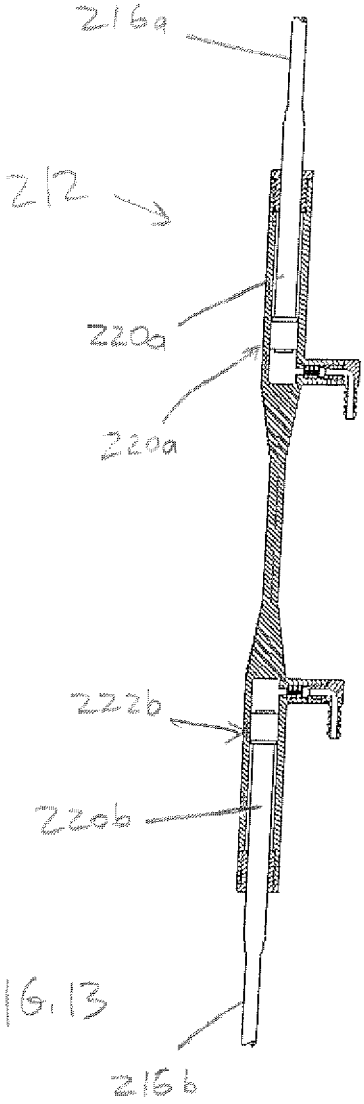
FIG. 13 is a longitudinal cross-section view of the growing rod assembly of FIG. 12.
Figure 12:
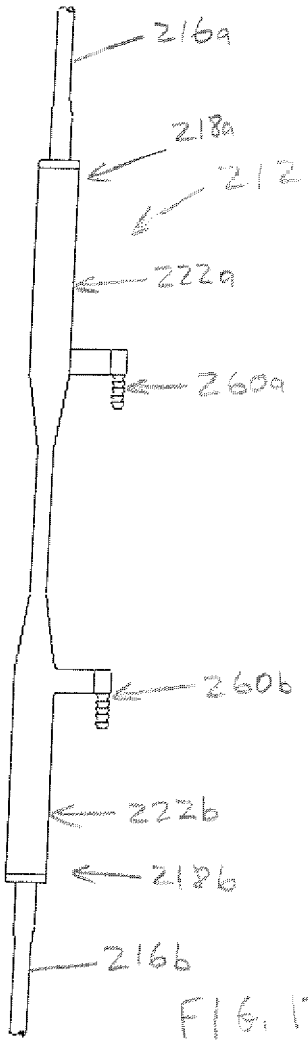
FIG. 12 is a rear view of a growing rod assembly of a growing rod system according to a second example embodiment of the present invention, showing back-to-back fluid actuators connected by a connecting rod.
Figure 15:
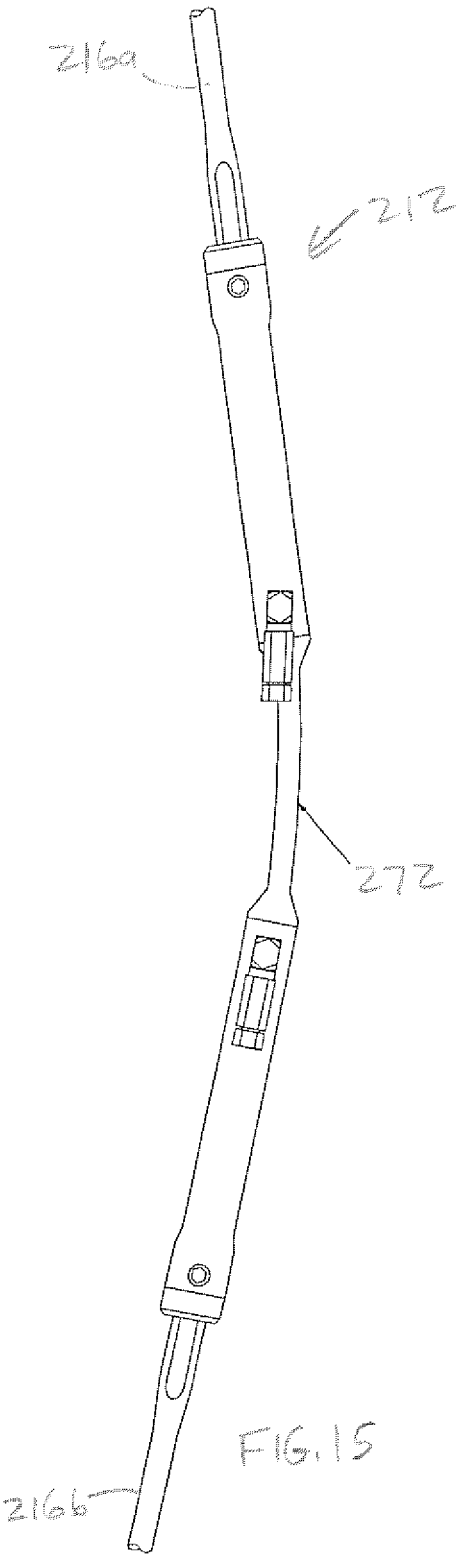
FIG. 15 shows the growing rod assembly of FIG. 14, with the connecting rod bent into a curved configuration.
Figure 14:
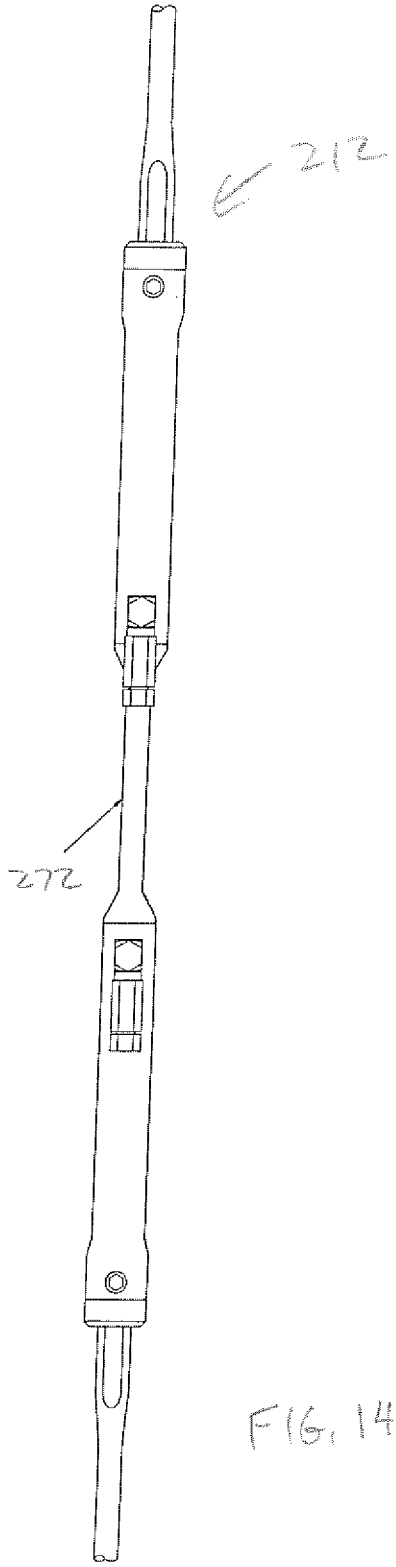
FIG. 14 is a right side view of the growing rod assembly of FIG. 12.
Figure 16:
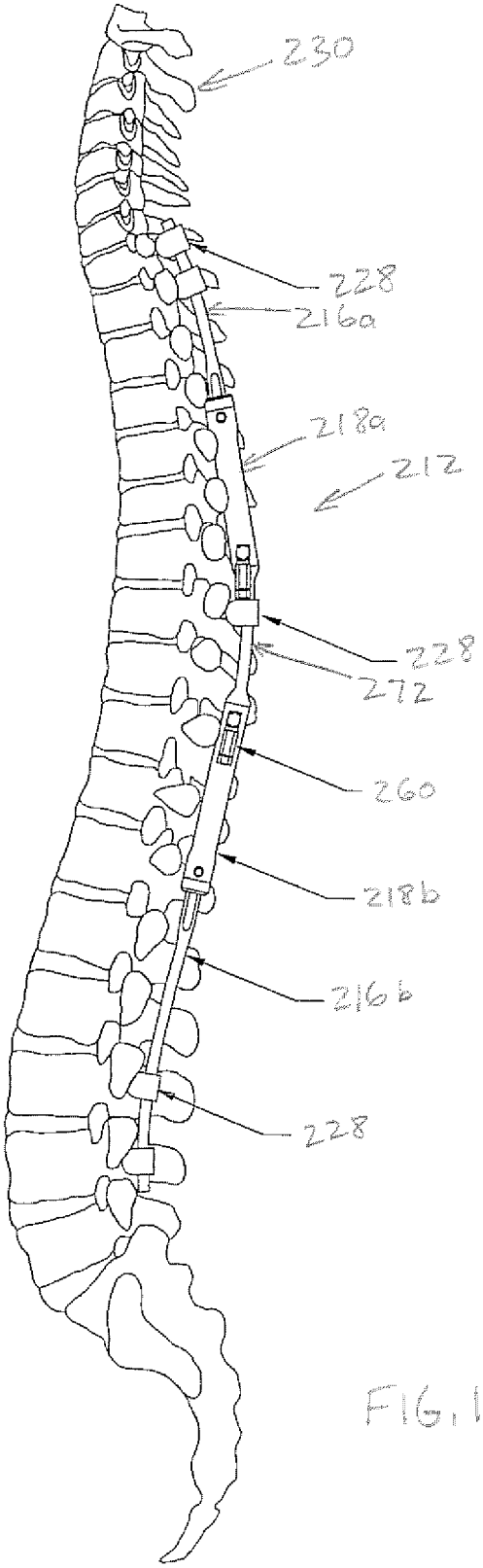
FIG. 16 shows the growing rod assembly of FIG. 15 mounted to a spine.

The piston-cylinder actuator 118 includes at least one internal seal 132 designed to sustain the system operating pressure and prevent leakage of the actuating fluid. In the depicted embodiment, for example, a sleeve seal 132 (e.g., made of a polymer material) is mounted onto the piston 120 for engagement with the inner surface of the cylinder wall 124 (see FIG. 5). In alternative embodiments, the seal is provided by a series of O-rings (e.g., the two O-rings 132a of FIG. 11) or by other conventional sealing elements known in the art.

In addition, the growing rod assembly 112 can include an anti-rotation mechanism to prevent relative rotational motion between the piston 120 and the cylinder 124. Such rotation can cause binding of the piston 120 and the cylinder 122, damage to the seal 132, and damage to other internal mating surfaces of the piston and the cylinder. For example, the anti-rotation mechanism can include mating keyed features of the piston 120 and the cylinder 122 to prevent relative rotational motion. In the depicted embodiment, the cylinder 122 has an end 134 forming an opening 136 through which the piston 120 extends into the cylinder bore 126. The piston 120 includes one or more male splines 138 (ribs, ridges, posts, pins, etc.) extending outwardly (e.g., radially) from it and the piston-receiving opening 136 includes one or more female splines 140 (recesses, notches, channels, etc.) formed in the cylinder end 134 such that the shape and size of the piston-receiving opening generally correspond to the cross-sectional geometry of the splined piston (see FIGS. 6 and 7). That is, the female splines 140 of the piston-receiving opening 136 receive the male splines 138 of the piston 120 to prevent relative rotation between the piston 120 and the cylinder 124, while still permitting easy longitudinal relative motion between them. In an alternative embodiment, the anti-rotation mechanism includes female splines formed in the piston and male splines that extend into the piston-receiving opening and mate with the female splines to prevent relative rotation. And in other alternative embodiments, the anti-rotation mechanism includes other mating keyed elements of the piston and the cylinder such as sections with polygonal or other regular or irregular shapes, longitudinal slots with corresponding guide pins, and the like.

The end 134 of the cylinder 122 can be provided by an endcap 142 that forms the piston-receiving opening 136 (see FIG. 6). The endcap 142 can be held in place by for example conventional fasteners such as set screws 144. Also, a guide bushing (not shown), made for example of a polymer, can be mounted at the end 134 of the cylinder 122 (e.g., within the cylinder bore 126) to contact the piston 120 and reduce the likelihood of the piston and the cylinder binding.

Figure 8:
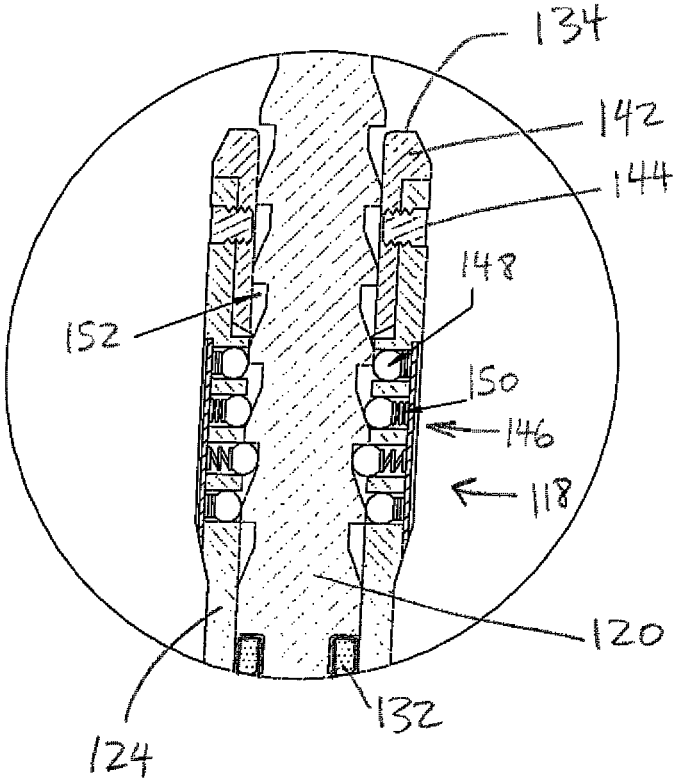
FIG. 8 is a detail view of a portion of the piston-cylinder actuator of the growing rod assembly of FIG. 5, showing details of an anti-retraction mechanism.

To prevent the unintentional collapse of the rod segments 116 in the event of system pressure loss, hysteresis, or fluid leakage, the growing rod assembly 112 can include an anti-retraction mechanism that incrementally blocks the piston 120 from retracting into the cylinder bore 126. For example, the anti-retraction mechanism can include at least one mechanical catch on the piston 120 and at least one mechanical catch on the cylinder 122 that selectively engages the piston catch to prevent collapse of the rod segments 116 while permitting their expansion. As shown in FIG. 8, the anti-retraction mechanism 146 of the depicted embodiment includes a series of male catches 148 that are biased by spring elements 150 into engagement with a series of female catches 152. The male catches 148 can be provided by one or more ball bearings (e.g., 2.0 mm diameter) that are biased radially inward by helical compression springs 150, with the ball bearings and the springs received at least partially within recesses in the inner surface of the cylinder wall 124. And the female catches 152 can be provided by a series of notches in at least one of the male splines 138 of the piston 120, with the notches each including a ramped surface to permit rod segment 116 expansion and a catch surface to prevent rod segment collapse in the opposite direction. The longitudinal spacing of the ball bearings 148 and the notches 150 can be selected such that the block to collapse of the rod segment 116 occurs in for example about 0.5 mm increments.

In alternative embodiments, the anti-retraction mechanism includes ball bearings biased outwardly from the piston and cooperating notches formed in an inner surface of the cylinder wall, one spring is provided for biasing several of the ball bearings, different male catch elements are provided instead of ball bearings, and/or a linear ratchet-and-pawl mechanism is provided to prevent collapse of the rod segments back into the cylinders.

In another alternative embodiment, the anti-retraction mechanism includes at least one spring element (e.g., a helical compression spring) that is housed in the cylinder and that longitudinally biases the piston to force the rods segments in opposite directions to accomplish rod expansion. The actuating fluid is on the side of the piston opposite from the spring to provide the stop for incremental expansion by selectively being slowly released from the opposite side of the piston from the spring. Thus, in this alternative embodiment, an actuator connector is positioned at the opposite end of the cylinder from in this embodiment. A control assembly is operated to allow the incremental release of the fluid, under the pressure of the spring, through the actuator connector and out of the cylinder to expand the growing rod assembly. And the fluid remaining in the cylinder, instead of being used to expand the growing rod assembly, is used to prevent rod collapse.

In addition, the cylinder 118 includes a conventional fluid-line connector 160 through which the pressurized actuating fluid enters the cylinder bore 126. The actuator connector 160 can be provided by a frictional connector, a flared screw-nut connector, or the like. The cylinder 118 can also include a conventional one-way check valve 162 located between the actuator connector 160 and the cylinder bore 126 to provide pressure relief and to prevent fluid backflow into the fluid supply assembly 114.

Figure 10:
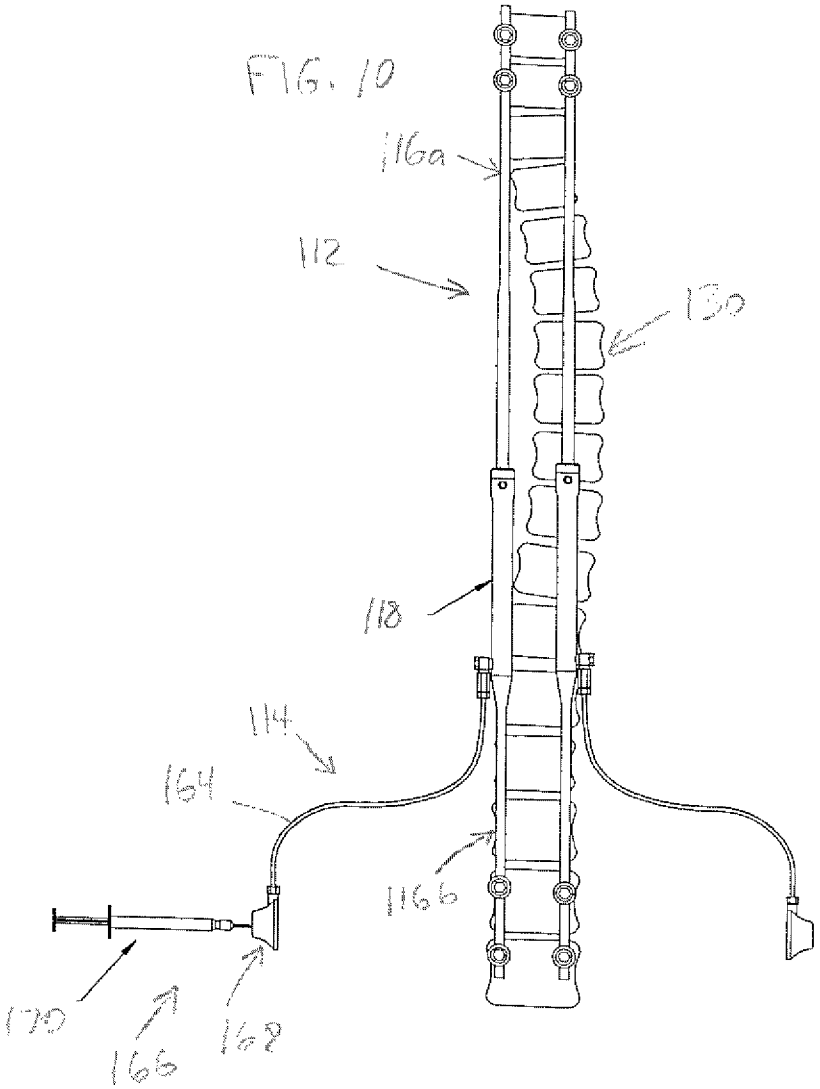
FIG. 10 shows the growing rod system and spine of FIG. 9 with the growing rod assembly lengthened to a second position.
Figure 9:
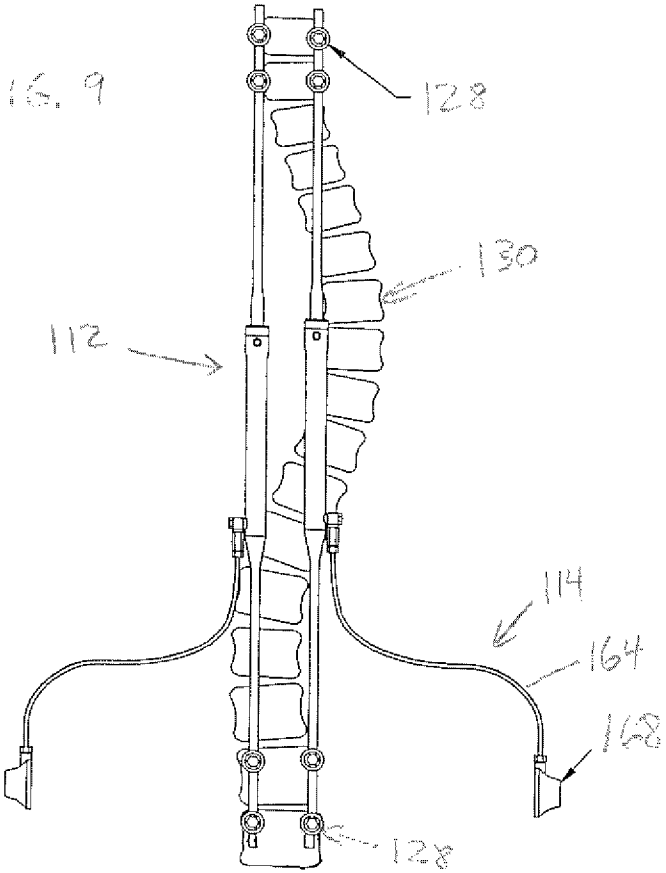
FIG. 9 shows the growing rod system of FIG. 1 mounted to a spine and shown in a first position.

Having described details of the growing rod assembly 112, details of the fluid supply assembly 114 will now be described with reference to FIGS. 4, 9, and 10. Each fluid supply assembly 14 includes at least one fluid line 164 and at least one fluid delivery device 166. Each growing rod assembly 112 can have a dedicated fluid supply assembly 114 or they can share one or more fluid supply assemblies.

The exact pressure requirements for rod segment 116 expansion can vary based on the particular design of the growing rod system 110 and can be selected based on the force required to correct a particular deformity. Reports in the current literature suggest a force of or less than about 200 Newtons is sufficient to provide for adequate expansion and incremental deformity correction. The growing rod system 110 of this embodiment can be operated at pressures of less than about 1,000 psi to provide about 350 Newtons of longitudinal expansion force with a nominal cylinder bore 126 of about 8.0 mm. However, as normal growth occurs and the spine elongates, a low or negative pressure within the cylinder 122 can result in a condition that will generally require little to no system pressure for expansion.

The fluid lines 164 supply the actuating fluid that powers the fluid actuators 118 of the growing rod assemblies 112. The fluid lines 164 are connectable at one end to the actuator connectors and at the opposite end to the fluid delivery device 166. The one-way check valve 162 in the fluid actuator 118 provides pressure relief and prevents backflow from the actuator into the fluid supply lines 164. The fluid lines 164 are provided by flexible tubing, hosing, or the like, with for example a minimum diameter of about 0.5 mm to about 2.0 mm to handle pressures of about 0.0 psi to about 1,000 psi. The fluid lines 164 are sterile and made of a biocompatible material so that they can be tunneled under the skin during emplacement of the growing rod assembly 112.

In the depicted embodiment, each fluid delivery device 166 includes an access port assembly 168 that is connectible to the respective fluid line 164 and that is operably engagable through the skin by a fluid pump 170. The access ports 168 are sterile and made of a biocompatible material so that they can be emplaced just under the surface of the skin and subcutaneous tissues. Segments of the fluid lines 164 that are to be placed near the access ports 168 can be coated with an antibiotic silicone rubber or plastic. A variety of subcutaneous access ports are currently available that can withstand system pressures of up to about 300 psi. As noted above, the design pressure of typical commercial embodiments can be up to about 1,000 psi, which is higher than what known subcutaneous access ports can safely withstand. So depending on the system pressure of a given design, the access ports 168 may need to be adapted to be capable of withstanding higher pressures. Alternatively, the growing rod system 100 can be designed to operate at lower pressures so that commercially available access ports can be used.

The fluid pump 170 of the depicted embodiment is a manually powered, external (to the body), piston-cylinder mechanism that is similar to a conventional syringe. The manual external pump 170 has an internal bore with a size (e.g., 1.0 mm to about 3.0 mm diameter) to provide actuating pressures (e.g., about 0.0 psi to about 1,000 psi) and volumetric flow (e.g., less than about 0.2 cubic cm) that produce the desired incremental expansion (e.g., about 0.5 mm to about 2.0 mm). The manual external pump 170 also includes a cannulated needle designed to insert through the skin and mate inside the subcutaneously placed access port 168. In embodiments in which the fluid pump 170 is provided by such a manual syringe-like device, the access ports 168 can be of a type similar to conventional vascular access ports that are accessed by cannulated large-bore needles. Because the actuation of the fluid pump 170 is manual, no additional controls are needed. Additional design details of the components of the fluid supply assembly 114 for delivering pressurized fluid to the fluid actuators 118 of the growing rod assemblies 112 will be understood by those of ordinary skill in the art of hydraulics and/or pneumatics.

In an alternative embodiment, the fluid pump is provided by a syringe-like manual external pump having a cannulated needle with threads. The access port has a section with threads that mate with the needle threads to provide a connection that allows delivery of the actuating fluid to the fluid actuator at a pressure adequate for incremental expansion of the rod segments. The access port can be implanted entirely subcutaneously or its threaded section can extend out of the skin. In other alternative embodiments, the fluid pump is provided by other manually actuated, external, conventional or modified hypodermic syringes.

In yet another alternative embodiment, the fluid pump is provided by a non-manually powered external pump (e.g., powered by an electric motor or an air compressor) that delivers actuating fluid from an external fluid reservoir. The electric pump provides fluid pressurization for the fluid actuators and can be provided by a hydraulic or hybrid pneumatic/hydraulic pump. The electric pump supplies pressurized fluid to the actuating cylinders at for example a maximum pressure of about 1000 psi and at a flow volume that causes incremental linear expansion of the rod segments at a rate of about 0.5 mm to about 2.0 mm per month. This may be accomplished with a high-pressure, low-output, positive displacement-type pump powered by DC electric or stepper motors, piezioelectric motors or linear actuators, or externally coupled magnetic drives. In such external electric pump embodiments, an external fluid line extends from the external pump and is removably connectable to the access port. The access port can be implanted with a fluid line connector extending out of the skin, or it can be entirely subcutaneous and accessed for example by a needle connected to the external fluid line. For example, the access port and the external fluid line may include mating connectors to allow delivery of the fluid by the external pump from the fluid reservoir to the fluid actuator at pressures adequate for incremental expansion of the actuator. In addition, in such external electric pump embodiments, the fluid delivery assembly includes a control system that can be a part of or a separate component from the fluid pump. The control system includes a power supply that can be provided by batteries, a power cord for electrically connecting to an electric outlet, a solar cell, etc. The control system also includes an on-off switch and/or other conventional controls for controlling the external fluid pump.

Having described details of the growing rod system 110, methods of surgically implanting and using the system will now be described with reference to FIGS. 9 and 10. A single growing-rod assembly 112, or dual (or more) growing-rod assemblies, may be used according to surgeon preference and/or as required for the desired correction. For illustration purposes only, the implanting method will be described in connection with dual growing-rod assemblies.

An incision is made above and below the deformity and carried through the subcutaneous tissues, fascia, and paraspinous musculature. Then the posterior elements of the spine are identified. The foundation sites for two growing rods assemblies 112 are selected using standard open techniques for posterior spinal instrumentation. The rod segments 116, which are typically provided in a linear configuration, can be bent into a curved configuration using conventional contouring techniques and tools. For example, the rod segments 116 can be bent into a curve that generally conforms to the curvature of a normal upper thoracic and lumbar spine. If the fluid lines 164 are not provided already connected to the fluid actuators 118, connection is now made. The two growing rod assemblies 112 are then placed below the skin and muscle fascia, and then connected to the foundation sites using standard spinal growing rod fixation techniques and mounting hardware 128. The growing rod assemblies 112 can each be mounted only at the ends of the rod segments 116 above and below the deformity, or they can be additionally mounted at the cylinder to the mid-spine (i.e., at an intermediate location of the deformity, that is, between the top and bottom of the deformity).

The access port 168 is then installed just beneath the skin and subcutaneous tissues at a suitable site such as the flank. Implanting in the flank of the body is cosmetically acceptable and allows easy access to the port 168 with minimal risk of local infection. The fluid lines 164 for powering the fluid actuators 118 are brought up through the fascia and tunneled under the skin to adjacent the access port 168. Then the fluid lines 164 are connected to the access port 168.

Alternatively, the fluid line can be installed exiting out through the skin and plugged, with the unplugged end of the fluid line serving as the access port. However, standard precautions would need to be taken on an ongoing basis to prevent wound complications at the site where the fluid line extends through the skin.

To use the growing rod system 110, the fluid pump 170 is operably coupled to the access port 168 and actuated to force the actuating fluid through the fluid lines 164 and into the cylinder bore 126. The pressurized fluid forces the piston 120 to reciprocate, thereby causing the rod segments 116 to move farther apart, i.e., to expand. For example, FIG. 9 shows the rod segments 116 in a first position mounted to a young patient's spine 130 with a 50-degree curve. And FIG. 10 shows the same rod segments 16 expanded to a second position mounted to the same spine 130 after aging and spinal growth and after the rod segments have been expanded by about 15 percent. In practice, this method is repeated a plurality of times to incrementally expand the rod segments 116 between the depicted first and second positions.

FIGS. 12-16 show a growing rod assembly 212 of a growing rod system according to a second example embodiment. The growing rod system is similar to that of the first example embodiment in that it includes a growing rod assembly 212 and a fluid delivery assembly (not shown). In this embodiment, however, the growing rod assembly 212 includes first and second fluid actuators 218a and 218b that are generally aligned to extend first and second rod segments 216a and 216b in opposite directions along the spine 230. In the depicted embodiment, for example, the fluid actuators 218a and 218b are provided by piston-cylinder actuators that are oriented with their respective pistons 220a and 220b extendible in opposite directions along the spine 230. The first rod segment extends 116a longitudinally from the first piston 220a and the second rod segment extends 116b longitudinally from the second piston 220b in an opposite direction.

The fluid actuators 218a and 218b each have an actuator connector 260a and 260b, respectively, to which two fluid lines (not shown) are connected. Two access ports (not shown) can be provided for connecting to the fluid lines (and thus to the actuator ports 260a and 260b) in a one-to-one relationship, thereby providing for independent operation of and variable fluid inflow to the two fluid actuators 218. A single fluid pump (not shown) can be used to sequentially and selectively expand the first rod segment 216a and/or the second rod segment 216b. In alternative embodiments, both fluid lines are split from a single feed line (not shown) that connects to a single access port.

The two cylinders 222a and 222b of the fluid actuators 218a and 218b are connected together in an end-to-end arrangement (with the respective pistons 220a and 220b extendible in opposite directions) by a connector rod 272. The connector rod 272 allows standard spinal mounting hardware 228 to be used to attach the growing rod assembly 212 to a foundation site located in the mid-spine (e.g., at the apex of the thoracic curve of the spine). This in turn allows for differential expansion in the lumbar and thoracic regions of the spine 230 by selectively and differentially expanding the first and/or second rod segments 216a or 216b. This also provides for more control in correcting rotational deformities in the spine 230.

In addition, the connector rod 272 can be made of a material with sufficient ductility to permit the connector rod to be plastically deformed and contoured into a curve to generally conform to the natural curvature of the spine 230 and also sufficiently strong to aid in correction of the spinal deformity. Contouring of the connector rod 272 (as well as of the rod segments 216) can be done using currently available rod contouring tools and techniques. Suitable materials for making the connector rod 272 includes, for example, stainless steels, nickel chromium alloys, titanium alloys, or PEEK or other high-strength thermoplastics. Furthermore, the connector rod 272 and the cylinders 222 can be integrally fabricated together as a single piece or these parts can be fabricated separately and attached together using conventional manufacturing techniques.

The methods of installing and using the growing rod system of this embodiment are similar to those of the first embodiment. For this embodiment, however, the installation method includes the step of affixing the connector rod 272 to the mid-spine using mounting hardware 228. And the use method includes the step of selectively operating the fluid delivery assembly 214 to actuate the first fluid actuator 218a and/or the second fluid actuator 218b to produce the desired expansion in the lumbar and/or thoracic regions of the spine 230.

FIGS. 17-26 show a growing rod system 310 according to a third example embodiment. The growing rod system 310 is similar to that of the first example embodiment in that it includes two growing rod assemblies 312 and two fluid delivery assemblies 314. Thus, each fluid delivery assembly 314 includes a fluid pump 370 connected to a fluid line 364, which in turn is connected to an actuator connector 360. Also, each growing rod assembly 312 includes a fluid actuator 318 that is operable to extend first and second rod segments 316a and 316b (collectively the "rod segments 316") in opposite directions along the spine 330. In the depicted embodiment, for example, the fluid actuator is 318 is provided by a piston-cylinder actuator with the first rod segment 316a extending longitudinally from the piston 320 and the second rod segment 316b extending longitudinally from the cylinder 322.

In contrast to the above-described embodiments, however, the fluid actuator 318 is sagittally curvilinear. Thus, in the depicted embodiment with the piston-cylinder fluid actuator 318, the piston 320 and the cylinder 322 are both curved in the sagittal plane. In addition, one or both of the rod segments 316 can be curved in the sagittal plane. The curvature of the fluid actuator 318 is typically selected to generally conform to the curvature of the normal spine 330 (i.e., the desired post-treatment curvature). For example, the radius of curvature of the piston 320 and of the cylinder 322 is typically in the range of about 20 cm to about 50 cm, and being within the range of about 25 cm to about 35 cm has shown particularly good results. The piston 320 and the cylinder 322 have the same constant radius of curvature, and the cylinder has a precise internal bore 326 to permit the curved piston to reciprocate smoothly within the curved bore. Accordingly, the piston 320 telescopes in a sagittally curvilinear fashion relative to the internal bore 326 of the hollow cylinder 322. This allows for a curvilinear expansion of the growing rod assembly 312 that closely (or at least better) approximates the natural curve of the spine 330 (see FIG. 26).

The curvilinear piston-cylinder actuator 318 can be constructed using high-precision manufacturing methods and equipment/tools. For example, the curved piston 320 and cylinder 322 can be formed by precision manufacturing techniques such as direct metal laser sintering, centrifugal or vacuum pressure investment-casting, or powder casting, followed by flexible honing and/or electropolishing and electroplating to achieve the desired smoothness of their mating curved surfaces. Testing and experimentation have indicated that, for a piston 320 and a cylinder bore 326 each having a constant radius of curvature of about 40 cm, a separation/clearance between the piston outer surface and the cylinder inner surface of about 101.6 microns (0.004 inch) is desired to minimize leakage and binding. Additional testing and experimentation have indicated that, in order to achieve this tight clearance, a surface finish (i.e., smoothness) of no more than about 32 microns (0.001259 inch) is desired for the mating surfaces of the curved piston 320 and cylinder 322. Using the above-mentioned high-precision manufacturing techniques, the curved piston 320 and cylinder 322 can be manufactured with an about 8-micron (0.000314-inch) surface finish, which is smooth enough to maintain the piston-cylinder actuator seals during working pressures of up to 3000 psi.

Figure 23:
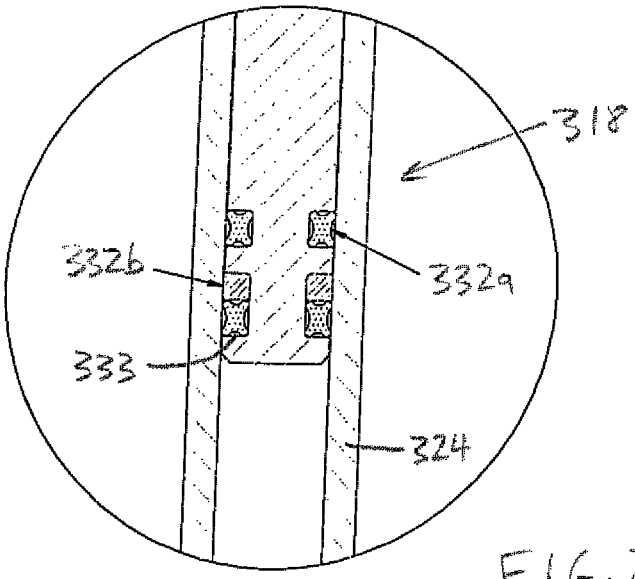
FIG. 23 is a detail view of a portion of a piston-cylinder actuator of the growing rod assembly of FIG. 22, showing details of a sealing system.

In addition, the fluid actuator 318 of the depicted embodiment includes a different fluid sealing system. As shown in FIG. 23, the fluid actuator 318 includes a dual-quad sealing system including a series (e.g., at least two) of main ring seals 332a (e.g., X-ring seals) and at least one backing ring seal 332b (e.g., an O-ring seal). The ring seals 332a and 332b can be made of buna, VITON, silicon or another conventional seal material. The backing O-ring 332b is interposed between the two main ring seals 332a. In the depicted embodiment, for example, the backing O-ring 332b is positioned adjacent the trailing edge of one of the main X-ring seals 332a and within the same forward circumferential groove 333, while the other one of the main X-ring seals is in the rear circumferential groove.

Figure 24:
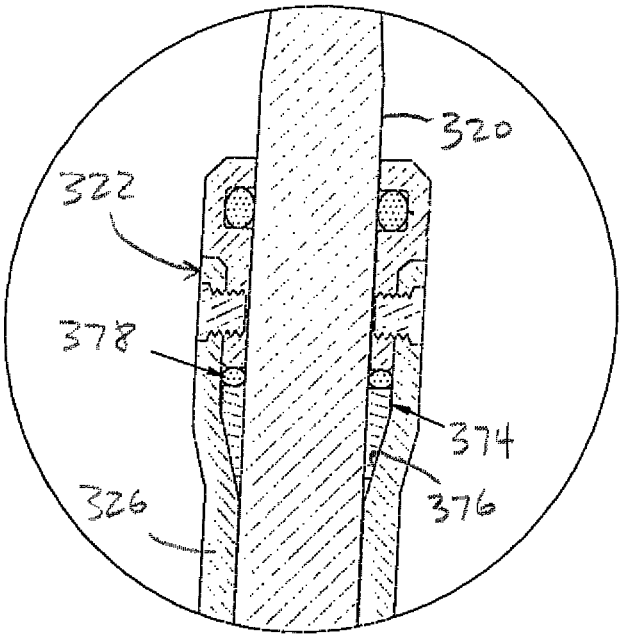
FIG. 24 is a detail view of a portion of a piston-cylinder actuator of the growing rod assembly of FIG. 22, showing details of an anti-retraction mechanism.
Figure 25:
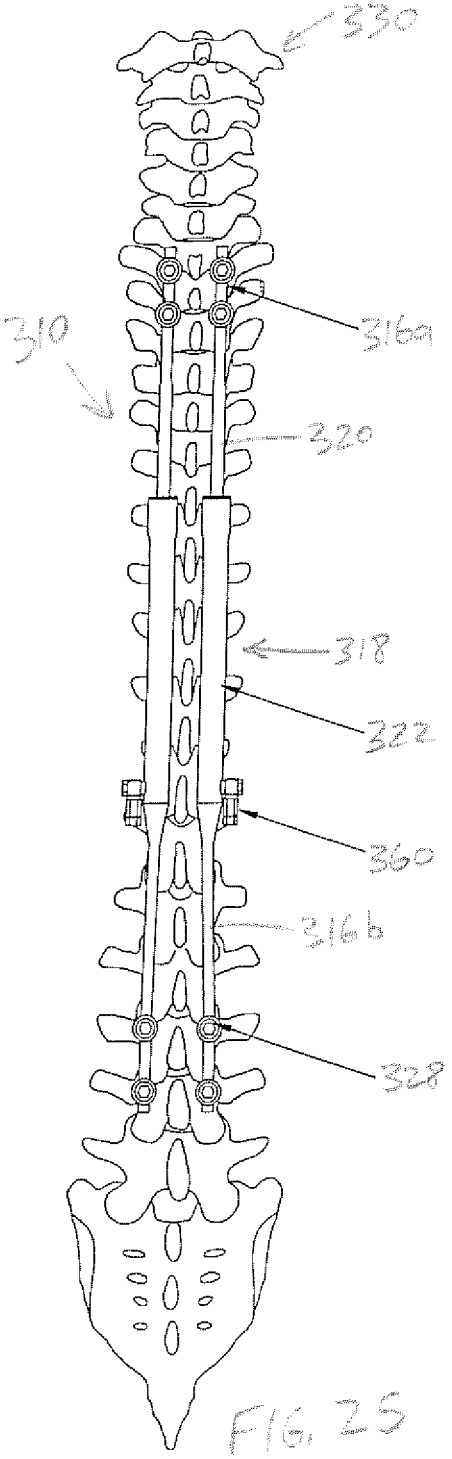
FIG. 25 is a rear view of the growing rod system of FIG. 17 mounted to a spine.
Figure 26:
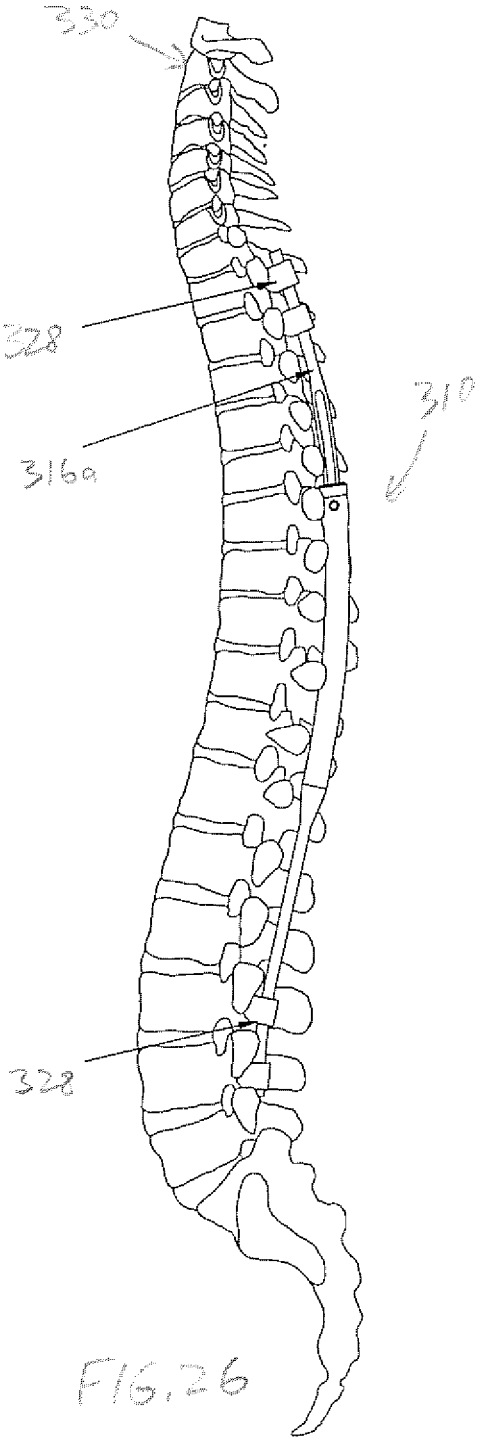
FIG. 26 is a left side view of the growing rod system and spine of FIG. 17.

Furthermore, the fluid actuator 318 of the depicted embodiment includes a different anti-retraction mechanism. As shown in FIG. 24, the anti-retraction mechanism includes a collet system to prevent rod collapse. The collet system can include at least one wedge 374 made of a rigid material such as a metal. For example, a single circumferential collar wedge can be provided or a plurality (i.e., two or more) partially-circumferential wedges (with flat or curved bases) can be provided. The wedges 374 are received in ramped recesses (e.g., notches or circumferential grooves) 376 in the cylinder wall 326. The cylinder 322 can have an outwardly flared section to accommodate the thickness of the wedges. The wedges 374 are configured so that they can be positioned within the recesses 376 and around the piston 320 in such a way that as the piston moves forward (outward from the cylinder 322), the wedges expand diametrically and there is no resultant interference between the piston and wedges, thus permitting easy sliding between them. As the piston 320 is retracted (back into the cylinder 322), however, the wedges 374 are collapsed diametrically relative to each other (due to the interference between the ramped surfaces of the wedges and the ramped surfaces of the recesses 376) resulting in interference between the base surfaces of the wedges and the outer surface of the piston, thus preventing further retraction. A resilient element 378 such as an O-ring, wave wire, elastic plug or bead, or the like is provided to keep the wedges 374 as close to the piston 320 as possible, thus eliminating significant retraction before engagement of the wedges and the piston.

Figure 17:
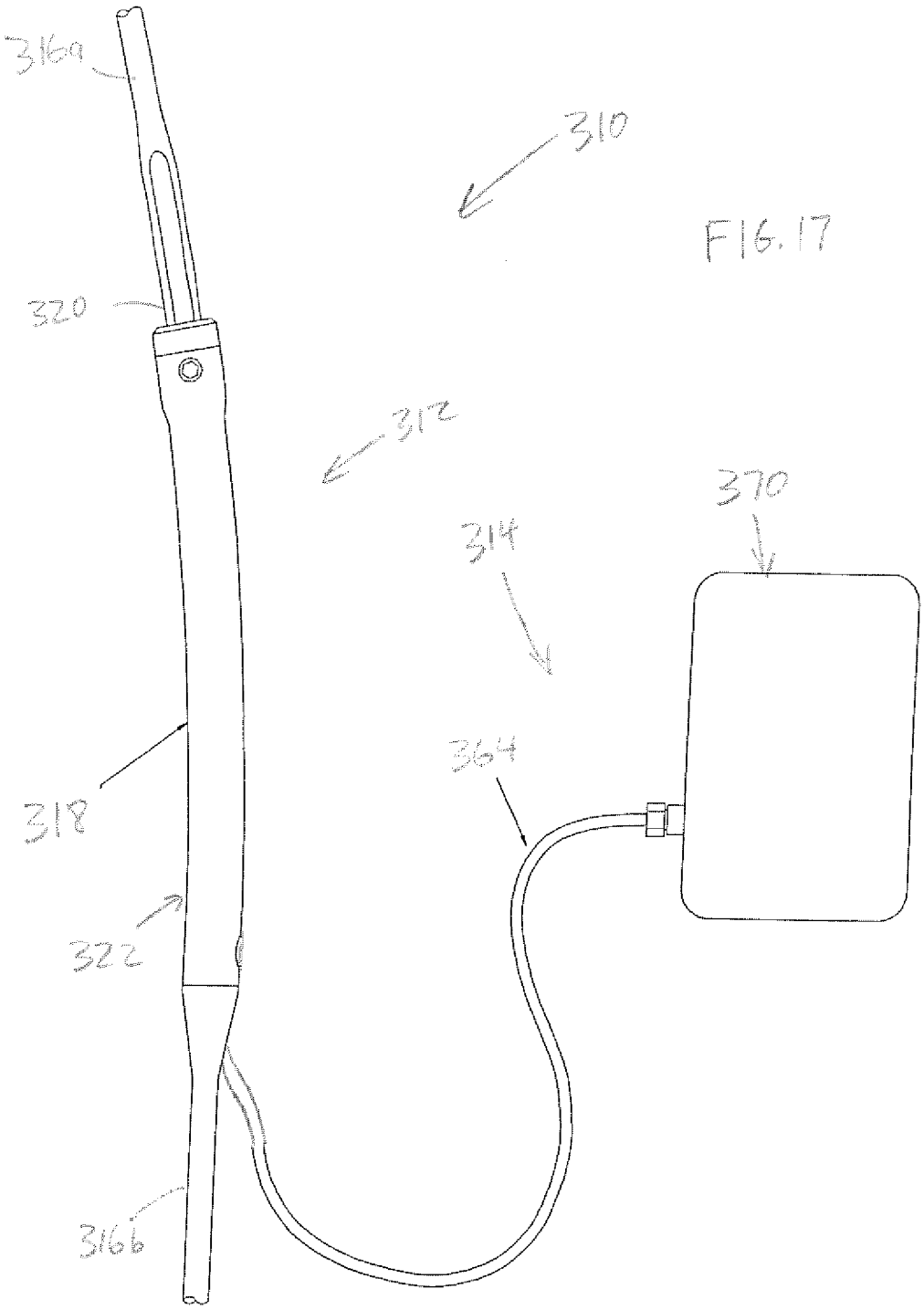
FIG. 17 is a left side view of a growing rod system according to a third example embodiment of the present invention, showing a curvilinear growing rod assembly and an internal fluid delivery assembly.
Figure 20:
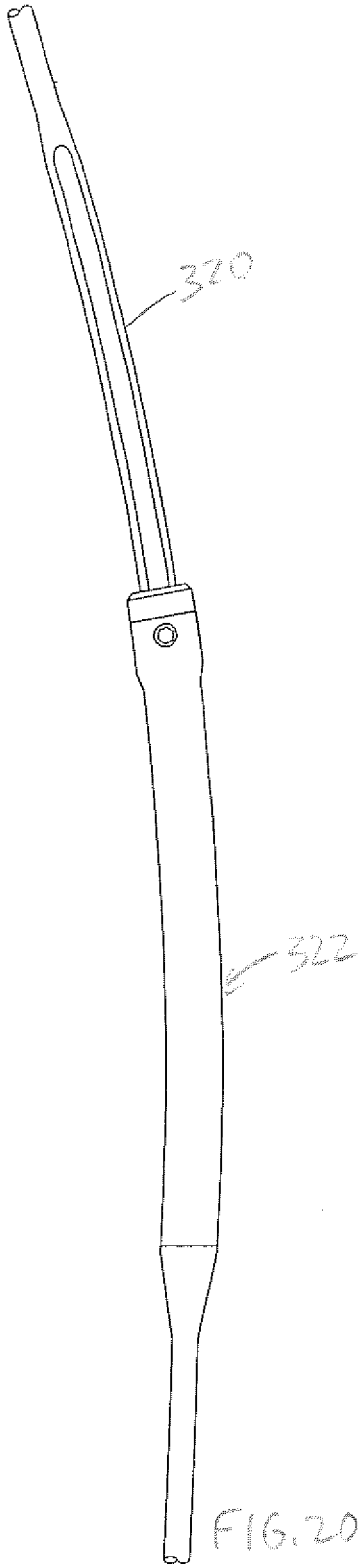
FIG. 20 shows the growing rod assembly of FIG. 19 in a second extended position.
Figure 19:
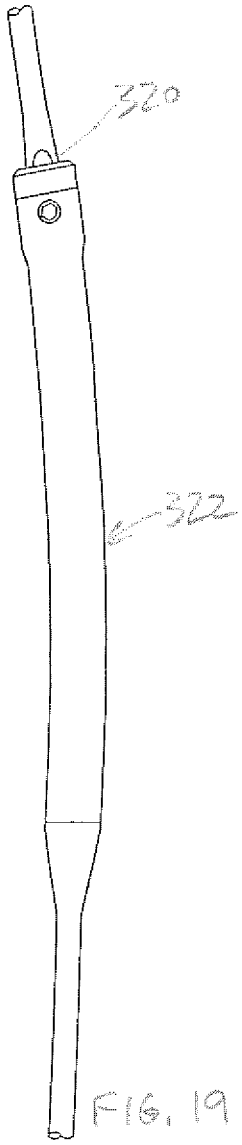
FIG. 19 is a left side view of the growing rod assembly of FIG. 18.
Figure 18:
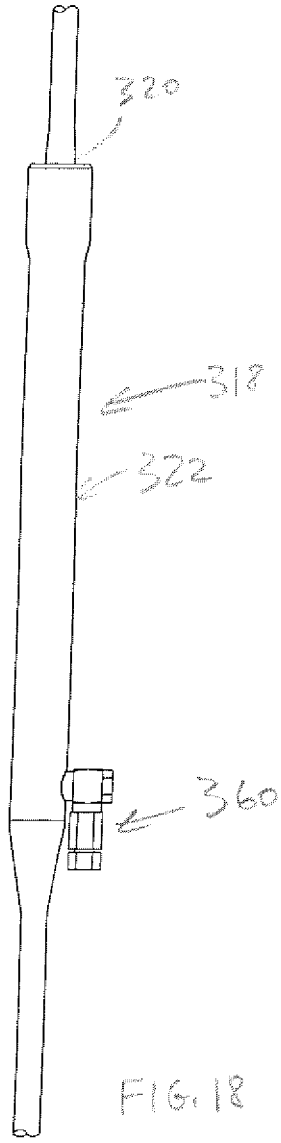
FIG. 18 is a rear view of the growing rod assembly of FIG. 17 shown in a first retracted position.
Figure 22:
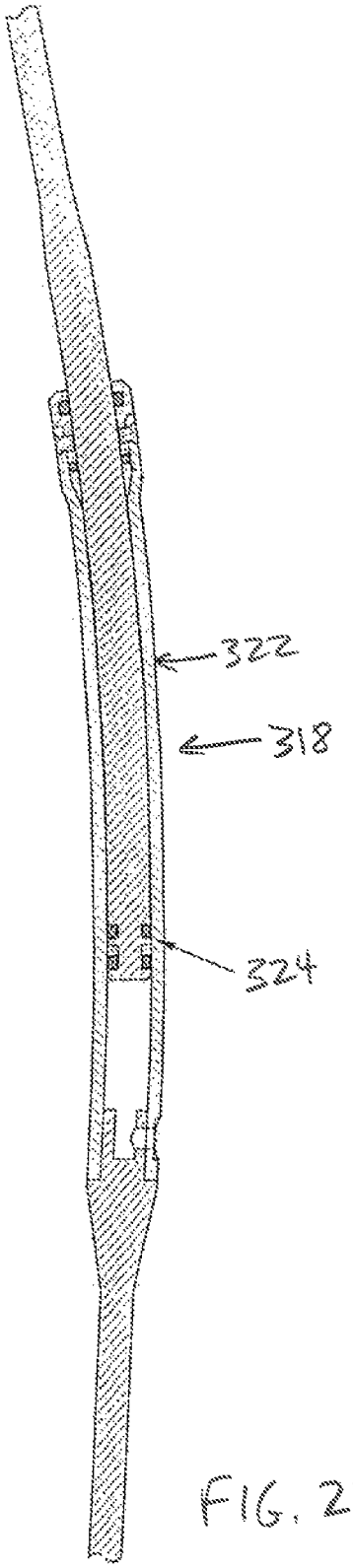
FIG. 22 is a longitudinal cross-section view of the growing rod assembly of FIG. 21.
Figure 21:
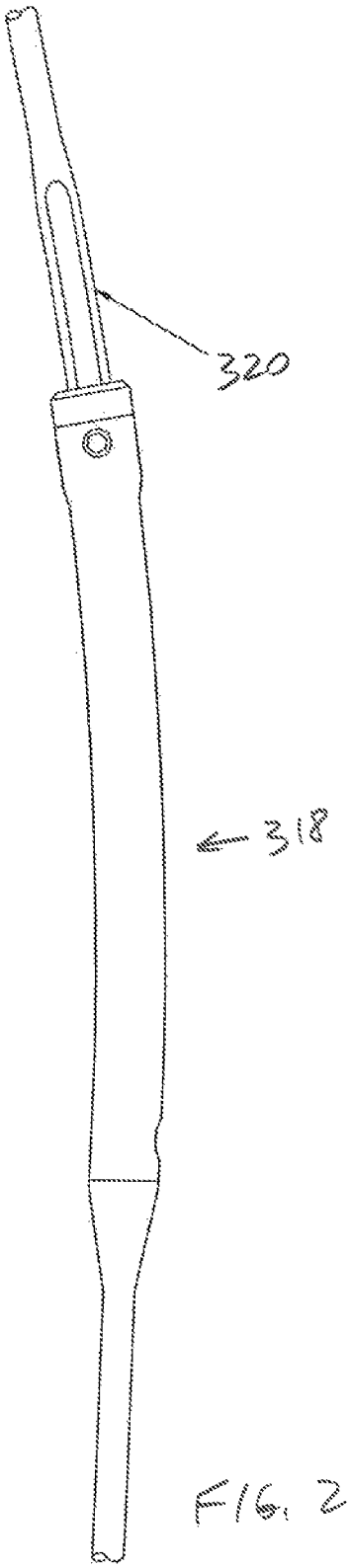
FIG. 21 shows the growing rod assembly of FIG. 19 shown in a partially extended position.

Moreover, the fluid delivery assembly 314 of the depicted embodiment is different from that of the above-described embodiments. As shown in FIG. 17, for example, the fluid pump 370 can be provided by an internal (to the body) fluid pump. This may be accomplished with a high-pressure, low-output, positive displacement-type pump powered by DC electric or stepper motors, piezioelectric motors or linear actuators, or externally coupled magnetic drives. Additionally, fluid could be delivered by use of a small volume of highly compressed gas within a small implanted reservoir which could be throttled through a remotely controlled microvalve apparatus. The internal pump 370 is connected directly to at least one of the growing rod assemblies 312 by the fluid lines 364. The associated valving, power supply, and fluid reservoir can be integral to the pump 370. The pump 370 can be encased in a bio-inert material and surgically implanted in the patient at the time of inserting the growing rod assembly 312 and the other components of the fluid delivery assembly 314. The pump 370 provides pressurization of the actuating fluid for the fluid actuator 318 and can be of a hydraulic or hybrid pneumatic/hydraulic design. In a typical commercial embodiment, the pump 370 supplies pressurized fluid to the fluid actuator 318 at a pressure of up to about 1000 psi and at a flow volume selected to cause continuous or incremental expansion of the rod segments 316 at a rate of about 0.5 mm to about 2.0 mm per month. Because the fluid pump is internal (i.e., implanted into the body), a subcutaneous access port is not included in this embodiment.

Additionally, the fluid delivery assembly 314 of this embodiment includes a control system (not shown) for controlling the actuation of the internal pump 370. For example, the control system can include an external remote control unit having a radiofrequency (RF) transmitter, an antenna, a microprocessor controller, control circuitry (for on/off functionality, fluid volume/rate control, low power warning, etc.), and a power supply. The power supply can be provided by one or more batteries, a power cord for electrically connecting to an electric outlet, a solar cell, etc. The control system also includes an internal control unit that the external control unit communicates with and controls. The internal control unit is implanted in the body and is included in or operably connected to the internal pump 370. The internal control unit includes an RF receiver, an antenna, a microprocessor controller, control circuitry (for on/off functionality, fluid volume/rate control, etc.), and a power supply. The power supply can be provided by for example one or more batteries. The transmitter, receiver, antennas, microprocessors, and control circuits are of a conventional type for sending and receiving RF signals to remotely controlled electronic devices.

In an alternative embodiment, instead a transmitter and a receiver, the external and internal control units each include a transceiver, thereby also permitting the internal control unit to communicate with the external control unit (e.g., to provide a low-power or low-pressure warning). In such embodiments, the internal control unit can include a pressure sensor for detecting the pressure of the actuating fluid in the fluid actuator, and the external control unit can include an output device for displaying the detected pressure. In other alternative embodiments, the control system includes magnetic controls (e.g., using magnetic signatures) for activating and deactivating the internal electric pump, as is known in the art.

The methods of installing and using the growing rod system 310 of this embodiment are similar to those of the first embodiment. For this embodiment, however, the use method includes the steps of forming a second incision in area of the body where the internal pump/control unit 370 is to be implanted. This area can be selected to be cosmetically acceptable and functionally inconspicuous (e.g., over the abdominal or lumbar region). The installation method also includes emplacing the internal pump/control unit 370 through the second incision and into the selected area, tunneling the fluid lines 364 below the skin and subcutaneous tissues to adjacent the internal pump/control unit, and connecting the fluid lines to the internal pump/control unit.

Figure 27:
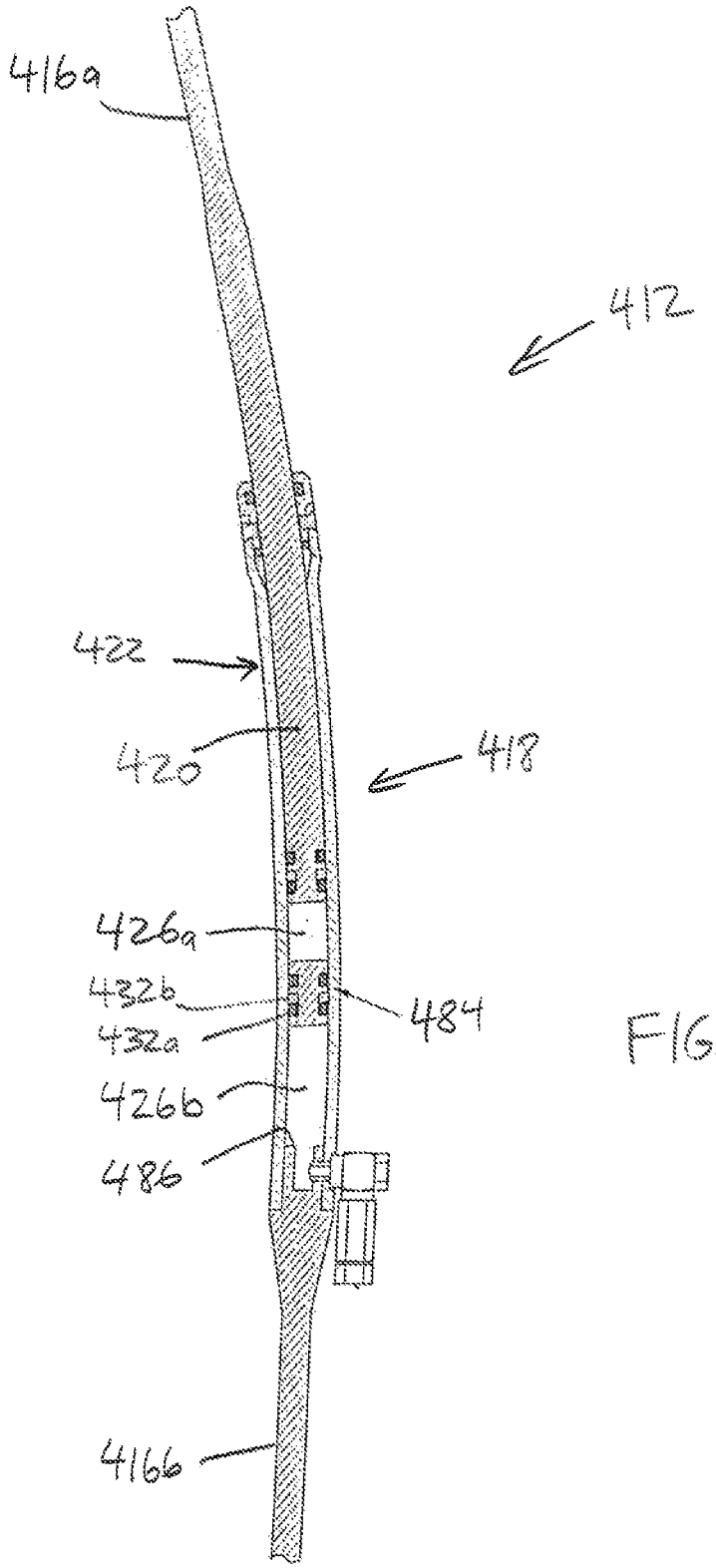
FIG. 27 is a longitudinal cross-sectional rear view of a growing rod assembly of a growing rod system according to a fourth example embodiment of the present invention, showing a gas-over-fluid shock absorber.

FIG. 27 shows a portion of a growing rod assembly 412 of a growing rod system according to a fourth example embodiment. The growing rod system is similar to that of the first example embodiment in that it includes two growing rod assemblies 412 and two fluid delivery assemblies. Thus, each growing rod assembly 412 includes a fluid actuator 418 that is operable to extend first and second rod segments 416a and 416b in opposite directions along the spine. In the depicted embodiment, for example, the fluid actuator 418 is provided by a piston-cylinder actuator with the first rod segment extending 416a longitudinally from the piston 420 and the second rod segment extending 416b longitudinally from the cylinder 422.

In addition, the fluid actuator 418 includes a fluid-over-fluid shock absorber that allows a slight longitudinal retractive motion of the piston 420 relative to the cylinder 422 and thereby dissipates impact forces. This small amount of motion can allow for some motion through the intervertebral disk, which may prevent premature or unwanted intervertebral fusion. In the depicted embodiment, the fluid-over-fluid shock absorber is provided by a floating core plug 484 and a volume of a compressible gas. The plug 484 slides within the bore of the cylinder 422 between the piston 420 and the cylinder endwall 486. The portion of the cylinder bore between the piston 420 and the plug 484 at any given position of the piston and the plug defines a first bore sub-space 426a. Likewise, the portion of the cylinder bore between the plug 484 and the cylinder endwall 486 at any given position of the plug defines a second bore sub-space 426b. The compressible gas is held within the first bore sub-space 426a and the actuating fluid is delivered under pressure into the second bore sub-space 426b. To maintain good sealing, the plug 484 includes a sealing system 432 such a dual-quad sealing system (e.g., with a series of X-ring seals 432a and at least one backing O-ring seal 432b) of the same type as in the third embodiment (see FIG. 23). The compressible gas can be provided by air, nitrogen, carbon dioxide, or another compressible gas known in the art. In typical commercial embodiments, a relatively small amount of the gas, such as about 0.5 $cm^3$ to about 2.0 $cm^3$, is contained in the first bore sub-space 426a. In operation, when the patient experiences a generally vertical force on the body (from walking, jumping, falling, etc.), the compressive gas in the first bore sub-space 426a will compress slightly, allowing the piston 420 to retract slightly back into the cylinder 422, thereby absorbing some of the force of the impact. In alternative embodiments, the fluid-over-fluid shock absorber is provided in a gas-over-gas, liquid-over-liquid, or liquid-over-gas configuration.

The several example embodiments, and the numerous alternative embodiments thereof, that are described herein include various different assemblies, elements, and features. Each of these various assemblies, elements, and features can be implemented in any other of the herein-described embodiments, unless the context or functional considerations obviously dictate otherwise.

Accordingly, the disclosed growing rod systems provide a number of advantages over the prior art designs. For example, prior art growing rods require frequent operative procedures, are expensive, require excessive resources, and place the patient at unnecessary risk. Certain of the disclosed growing rod systems allow for a single operative procedure for placement followed by periodic rod expansion performed in an office environment with a minimally invasive procedure. This alleviates the need for frequent operations, which would otherwise place the patient at risk of bleeding, infection, pulmonary complications, and frequent anesthetic exposure. In addition, the cost associated with surgical operating room time and overnight observation is eliminated.

Another advantage provided by certain of the disclosed embodiments is that they can be operated to perform slow incremental lengthening (at frequent intervals) and/or continuous lengthening, which is safer and more compatible with preserving normal growth. Additionally, the dual growing rod embodiments can be operated independently and in a coordinated fashion to provide more precise control of spinal deformity corrections. For example, in some instances correction may require expansion on the concave side of the deformity and compression on the convexity to allow straightening. To accomplish this, one of the fluid actuators can be expanded while the other is not, so that the stopped side may catch up before restarting the fluid actuator on that side again.

Yet another advantage provided by certain of the disclosed embodiments relates to the curvilinear design of the fluid actuator. Current systems include a purely linear expansion method, which does not account for the natural curvature of the spine. This in turn leads to hypokyphosis, junctional kyphosis, and increased risk of implant failure or bony pull-out with potential for resultant neurologic injury. Certain of the disclosed embodiments, however, include a curvilinear fluid actuator that provides for rod segment expansion conforming to the natural curvature of the spine.

It is to be understood that this invention is not limited to the specific devices, methods, conditions, or parameters of the example embodiments described and/or shown herein, and that the terminology used herein is for the purpose of describing particular embodiments by way of example only. Thus, the terminology is intended to be broadly construed and is not intended to be unnecessarily limiting of the claimed invention. For example, as used in the specification including the appended claims, the singular forms "a," "an," and "the" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein.

While the claimed invention has been shown and described in example forms, it will be apparent to those skilled in the art that many modifications, additions, and deletions can be made therein without departing from the spirit and scope of the invention as defined by the following claims.

What is claimed is:

1. A growing rod system for correcting a curvature or rotational orthopedic deformity of a curved spine of a body as the spine grows, comprising:

at least one growing rod assembly including a first longitudinal rod segment, a second longitudinal rod segment, and a fluid actuator that is operable to extend the first and second rod segments longitudinally relative to each other in opposite directions from a retracted position to an extended position, wherein the growing rod assembly is adapted to be mounted within the body to span the orthopedic deformity, wherein the fluid actuator is a piston-cylinder fluid actuator including a cylinder with an internal bore and a piston with a bore-received portion that telescopically reciprocates within the cylinder bore, wherein the first rod segment extends longitudinally from one of the piston or the cylinder and the second rod segment extends longitudinally from the other of the piston or the cylinder, wherein the bore-received piston portion and the cylinder bore of the piston-cylinder fluid actuator have a sagittal curve within a sagittal plane with a same, constant radius of curvature selected to generally conform to a desired post-treatment curvature of the spine within the sagittal plane, wherein the radius of curvature of the bore-received piston portion and the cylinder bore is maintained constant as the rod segments extend with respect to each other from the retracted position to the extended position to telescopically extend the bore-received piston portion and the cylinder bore with respect to each other along the sagittal curve within the sagittal plane to move portions of the spine relative to each other to form the desired post-treatment curvature of the spine, wherein the piston-cylinder fluid actuator includes an anti-rotation mechanism having mating keyed elements on the piston and the cylinder to prevent the piston and the cylinder from rotating relative to each other while permitting longitudinal extension relative to each other along the sagittal curve within the sagittal plane; and at least one fluid delivery assembly including at least one fluid line that is connected to the piston-cylinder fluid actuator to deliver an actuating fluid to the piston-cylinder fluid actuator to drive the piston-cylinder fluid actuator to extend the rod segments.

2. The system of claim 1, wherein the mating keyed elements include at least one male spline extending outwardly from one of the piston or the cylinder and at least one female spline extending inwardly into the other of the piston or the cylinder.

3. The system of claim 1, wherein the piston-cylinder fluid actuator includes a sealing system having at least two circumferential grooves formed in the piston, at least two main ring seals, and at least one backing ring seal, wherein one of the main seals is positioned in a rear one of the circumferential grooves and the other of the main ring seals and the backing ring seal are positioned together in a forward one of the circumferential grooves.

4. The system of claim 1, wherein the piston-cylinder fluid actuator includes a fluid-over-fluid shock absorbing mechanism including a floating plug that is slidably received within the cylinder bore between the piston and a bore endwall and that divides the bore into two sub-spaces, and a charge of a compressible fluid contained within one of the sub-spaces, wherein the actuating fluid is contained within the other one of the sub-spaces.

5. The system of claim 1, wherein the piston-cylinder fluid actuator includes first and second piston-cylinder fluid actuators configured in a back-to-back arrangement and connected by a connecting rod, wherein the connecting rod is made of a material that is sufficiently ductile to permit it to be bent into a curve, and wherein the connecting rod is adapted to be mounted to the orthopedic structure at an intermediate location of the orthopedic deformity.

6. The system of claim 5, wherein the piston-cylinder fluid actuators each include a cylinder with an internal bore and a piston that reciprocates within the cylinder bore, wherein the rod segments extend longitudinally from the respective pistons, the cylinders are configured in a back-to-back arrangement and connected by a connecting rod, the connecting rod is made of a material that is sufficiently ductile to permit it to be bent into a curve, and the connecting rod is adapted to be mounted to the orthopedic structure at an intermediate location of the orthopedic deformity.

7. A method of installing the growing rod system of claim 5, comprising:

bending the connecting rod into a curve;

mounting the first rod segment to the orthopedic structure at a site above the deformity; and mounting the second rod segment to the orthopedic structure at a site below the deformity.

8. The method of claim 7, further comprising:

mounting the connecting rod to the orthopedic structure at an intermediate site of the deformity.

9. A method of using the growing rod system of claim 5, comprising:

actuating the first piston-cylinder fluid actuator to extend the first rod segment; and actuating the second piston-cylinder fluid actuator to extend the second rod segment.

10. The system of claim 1, wherein the piston-cylinder fluid actuator is driven by an external fluid pump, and wherein the delivery assembly further includes a subcutaneous access port implantable within the body, connected to the fluid line, and connectable to or accessible by the external fluid pump.

11. A method of using the growing rod system of claim 10, comprising:

operably engaging the subcutaneous access port with the external fluid pump; and actuating the external fluid pump to actuate the piston-cylinder fluid actuator to extend the rod segments.

12. The system of claim 1, wherein the fluid delivery assembly further includes an internal fluid pump implantable within the body and connected to the fluid line.

13. The system of claim 1, wherein the [curved] piston and the [curved] cylinder are formed by a first precision manufacturing technique selected from the group consisting of direct metal laser sintering, centrifugal pressure investment-casting, vacuum pressure investment-casting, and powder casting, and wherein the curved piston and the curved cylinder have curved surfaces that mate with each other and are smoothened by a second precision manufacturing technique selected from the group consisting of flexible honing, electropolishing, and electroplating, wherein the curved piston and the curved cylinder are thereby formed with the mating curved surfaces sufficiently mating that they minimize binding and fluid leaking.

14. A growing rod system for correcting a curvature or rotational orthopedic deformity of a curved spine of a body as the spine grows, comprising:

at least one growing rod assembly including a first longitudinal rod segment, a second longitudinal rod segment, and a fluid actuator that is operable to extend the first and second rod segments longitudinally relative to each other[in opposite directions from a retracted position to an extended position], wherein the growing rod assembly is adapted to be mounted within the body to span the orthopedic deformity, wherein the fluid actuator is a piston-cylinder fluid actuator including a cylinder with an internal bore and a piston with a bore-received portion that [telescopically reciprocates] *moves* within the cylinder bore, wherein the first rod segment extends longitudinally from one of the piston or the cylinder and the second rod segment extends longitudinally from the other of the piston or the cylinder, wherein the bore-received piston portion and the cylinder bore of the piston-cylinder fluid actuator have a sagittal curve within a sagittal plane with a same, constant radius of curvature selected to generally conform to a desired post-treatment curvature of the spine within the sagittal plane, wherein the radius of curvature of the bore-received piston portion and the cylinder bore is maintained constant as the rod segments extend with respect to each other [from the retracted position to the extended position] to [telescopically] extend the bore-received piston portion and the cylinder bore with respect to each other along the sagittal curve within the sagittal plane[to move portions of the spine relative to each other to form the desired post-treatment curvature of the spine], wherein the piston-cylinder fluid actuator includes an anti-rotation mechanism having mating keyed elements on the piston and the cylinder to prevent the piston and the cylinder from rotating relative to each other while permitting longitudinal extension *of the piston and the cylinder* relative to each other along the sagittal curve within the sagittal plane, wherein the piston-cylinder fluid actuator includes an anti-retraction mechanism [includes mating catch elements on the piston and the cylinder] *configured* to prevent the piston and the cylinder from longitudinally retracting relative to each other while permitting longitudinal extension relative to each other; and at least one fluid delivery assembly [including at least one fluid line that is connected to the piston-cylinder fluid actuator] to deliver an actuating fluid to the piston-cylinder fluid actuator to drive the piston-cylinder fluid actuator to extend the rod segments.

15. The system of claim 14, *wherein the anti-retraction mechanism includes mating catch elements on the piston and the cylinder,* wherein the mating catch elements include a series of spring-biased bearings extending from one of the piston or the cylinder and a series of ramped notches formed in the other of the piston or the cylinder, wherein when a first one of the spring-biased bearings is positioned on a ramp portion of a first one of the ramped notches, a second one of the spring-biased bearings is positioned in a notch portion of a second one of the ramped notches.

16. The system of claim 14, *wherein the anti-retraction mechanism includes mating catch elements on the piston and the cylinder,* wherein the anti-retraction mechanism includes a collet mechanism in which the mating catch elements are provided by at least one base surface of at least one wedge received in at least one ramped recess of the cylinder and by an outer surface of the piston.

17. The system of claim 14, wherein the mating keyed elements include at least one male spline extending outwardly from one of the piston or the cylinder and at least one female spline extending inwardly into the other of the piston or the cylinder.

18. A growing rod system for correcting a curvature or rotational orthopedic deformity of a curved spine of a body as the spine grows, comprising:

at least one growing rod assembly including a first longitudinal rod segment, a second longitudinal rod segment, and a piston-cylinder fluid actuator including a cylinder with an internal bore and a piston with a bore-received portion that [telescopically reciprocates] *moves* within the cylinder bore, wherein the first rod segment extends longitudinally from one of the piston or the cylinder and the second rod segment extends longitudinally from the other of the piston or the cylinder, wherein the piston-cylinder fluid actuator is operable to extend the first and second rod segments longitudinally relative to each other[in opposite directions from a retracted position to an extended position], wherein the bore-received piston portion and the cylinder bore of the piston-cylinder actuator have a sagittal curve within a sagittal plane with a same, constant radius of curvature selected to generally conform to a desired post-treatment curvature of the spine within the sagittal plane, wherein the radius of curvature of the bore-received piston portion and the cylinder bore is maintained constant as the rod segments extend with respect to each other [from the retracted position to the extended position] to [telescopically] extend the bore-received piston portion and the cylinder bore with respect to each other along the sagittal curve within the sagittal plane[to move portions of the spine relative to each other to form the desired post-treatment curvature of the spine], wherein at least a portion of the first rod segment, the second rod segment, or both, is sagittally curved to generally conform to the desired post-treatment curvature of the spine, and wherein the curved piston, the curved cylinder, and the curved rod segment or segments are adapted to be mounted within the body to span the entire length of the orthopedic deformity, wherein the piston-cylinder fluid actuator includes an anti-rotation mechanism having mating keyed elements on the piston and the cylinder to prevent the piston and the cylinder from rotating relative to each other while permitting longitudinal extension *of the piston and the cylinder* relative to each other along the sagittal curve within the sagittal plane, wherein the mating keyed elements include [at least one male spline extending outwardly from one of the piston or the cylinder and at least one female spline extending inwardly into the other of the piston or the cylinder] (*i*) *one or more male splines and one or more corresponding female splines,* (*ii*) *sections with corresponding regular or irregular shapes, or* (*iii*) *longitudinal slots with corresponding guide pins*, wherein the piston-cylinder fluid actuator includes an anti-retraction mechanism [including mating catch elements on the piston and the cylinder] *configured* to prevent the piston and the cylinder from longitudinally retracting relative to each other while permitting longitudinal extension relative to each other[, wherein the mating catch elements include at least one spring-biased bearing extending from one of the piston or the cylinder and at least one ramped notch formed in the other of the piston or the cylinder, and wherein the anti-retraction mechanism includes a collet mechanism in which the mating catch elements are provided by at least one base surface of at least one wedge received in at least one ramped recess of the cylinder and by an outer surface of the piston]; and at least one fluid delivery assembly [including at least one fluid line and at least one fluid pump, wherein the fluid pump is positioned internal to or external to the body, and wherein the fluid line is connected to the piston-cylinder fluid actuator] to deliver an actuating fluid to the piston-cylinder fluid actuator to drive the piston-cylinder fluid actuator to extend the rod segments.

19. The system of claim 18, wherein the piston-cylinder fluid actuator includes a sealing system having at least two circumferential grooves formed in the piston, at least two main ring seals, and at least one backing ring seal, wherein one of the main seals is positioned in a rear one of the circumferential grooves and the other of the main ring seals and the backing ring seal are positioned together in a forward one of the circumferential grooves.

20. The system of claim 18, wherein the piston-cylinder fluid actuator includes a fluid-over-fluid shock absorbing mechanism including a floating plug that is slidably received within the cylinder bore between the piston and a bore endwall and that divides the bore into two sub-spaces, and a charge of a compressible fluid contained within one of the sub-spaces, wherein the actuating fluid is contained within the other one of the sub-spaces.

21. The system of claim 18, wherein the curved piston and the curved cylinder are formed by a first precision manufacturing technique selected from the group consisting of direct metal laser sintering, centrifugal pressure investment-casting, vacuum pressure investment-casting, and powder casting, and wherein the curved piston and the curved cylinder have curved surfaces that mate with each other and are smoothened by a second precision manufacturing technique selected from the group consisting of flexible honing, electropolishing, and electroplating, wherein the curved piston and the curved cylinder are thereby formed with the mating curved surfaces sufficiently mating that they minimize binding and fluid leaking.

*22. A growing rod system for correcting a curvature or rotational orthopedic deformity of a curved spine of a body as the spine grows, comprising:*

*at least one growing rod assembly including a first longitudinal rod segment, a second longitudinal rod segment, and a fluid actuator that is operable to extend the first and second rod segments longitudinally relative to each other, wherein the growing rod assembly is adapted to be mounted within the body to span the orthopedic deformity, wherein the fluid actuator is a piston-cylinder fluid actuator including a cylinder with an internal bore and a piston with a bore-received portion that moves within the cylinder bore, wherein the first rod segment extends longitudinally from one of the piston or the cylinder and the second rod segment extends longitudinally from the other of the piston or the cylinder, wherein the bore-received piston portion and the cylinder bore of the piston-cylinder fluid actuator have a sagittal curve within a sagittal plane with a same, constant radius of curvature, wherein the radius of curvature of the bore-received piston portion and the cylinder bore is maintained constant as the rod segments extend with respect to each other to extend the bore-received piston portion and the cylinder bore with respect to each other along the sagittal curve within the sagittal plane,*

*wherein the piston-cylinder fluid actuator includes an anti-rotation mechanism having mating keyed elements on the piston and the cylinder to prevent the piston and the cylinder from rotating relative to each other while permitting longitudinal extension relative to each other along the sagittal curve within the sagittal plane; and*

*at least one fluid delivery assembly to deliver an actuating fluid to the piston-cylinder fluid actuator to drive the piston-cylinder fluid actuator to extend the rod segments.*

*23. The system of claim 1, wherein the mating key elements comprise (i) one or more male splines and one or more corresponding female splines, (ii) sections with corresponding regular or irregular shapes, or (iii) longitudinal slots with corresponding guide pins.*

*24. The system of claim 22, wherein the mating key elements comprise one or more male splines and one or more female splines, wherein the one or more male splines comprise one or more ribs, ridges, posts, or pins, and wherein the one or more female splines comprise one or more recesses, notches, or channels.*

*25. The system of claim 22, wherein the mating key elements comprise (i) one or more male splines and one or more corresponding female splines, (ii) sections with corresponding regular or irregular shapes, or (iii) longitudinal slots with corresponding guide pins.*

*26. The system of claim 22, wherein the mating keyed elements include at least one male spline extending outwardly from one of the piston or the cylinder and at least one female spline extending inwardly into the other of the piston or the cylinder.*

*27. The system of claim 22, wherein the piston-cylinder fluid actuator includes a sealing system having at least two circumferential grooves formed in the piston, at least two main ring seals, and at least one backing ring seal, wherein one of the main seals is positioned in a rear one of the circumferential grooves and the other of the main ring seals and the backing ring seal are positioned together in a forward one of the circumferential grooves.*

*28. The system of claim 22, wherein the piston-cylinder fluid actuator includes a fluid-over-fluid shock absorbing mechanism including a floating plug that is slidably received within the cylinder bore between the piston and a bore endwall and that divides the bore into two sub-spaces, and a charge of a compressible fluid contained within one of the sub-spaces, wherein the actuating fluid is contained within the other one of the sub-spaces.*

*29. The system of claim 22, wherein the piston-cylinder fluid actuator includes first and second piston-cylinder fluid actuators configured in a back-to-back arrangement and connected by a connecting rod, wherein the connecting rod is made of a material that is sufficiently ductile to permit it to be bent into a curve, and wherein the connecting rod is adapted to be mounted to the orthopedic structure at an intermediate location of the orthopedic deformity.*

*30. The system of claim 29, wherein the piston-cylinder fluid actuators each include a cylinder with an internal bore and a piston that reciprocates within the cylinder bore, wherein the rod segments extend longitudinally from the respective pistons, the cylinders are configured in a back-to-back arrangement and connected by a connecting rod, the connecting rod is made of a material that is sufficiently ductile to permit it to be bent into a curve, and the connecting rod is adapted to be mounted to the orthopedic structure at an intermediate location of the orthopedic deformity.*

*31. A method of installing the growing rod system of claim 29, comprising:*

*bending the connecting rod into a curve;*

*mounting the first rod segment to the orthopedic structure at a site above the deformity; and*

*mounting the second rod segment to the orthopedic structure at a site below the deformity.*

*32. The method of claim 31, further comprising:*

*mounting the connecting rod to the orthopedic structure at an intermediate site of the deformity.*

*33. A method of using the growing rod system of claim 29, comprising:*

*actuating the first piston-cylinder fluid actuator to extend the first rod segment; and*

*actuating the second piston-cylinder fluid actuator to extend the second rod segment.*

*34. The system of claim 22, wherein the piston-cylinder fluid actuator is driven by an external fluid pump, and wherein the delivery assembly further includes a subcutaneous access port implantable within the body, and connectable to or accessible by the external fluid pump.*

*35. A method of using the growing rod system of claim 34, comprising:*

*operably engaging the subcutaneous access port with the external fluid pump; and*

*actuating the external fluid pump to actuate the piston-cylinder fluid actuator to extend the rod segments.*

*36. The system of claim 22, wherein the fluid delivery assembly further includes an internal fluid pump implantable within the body and connected to the fluid line.*

*37. The system of claim 22, wherein the piston and the cylinder are formed by a first precision manufacturing technique selected from the group consisting of direct metal laser sintering, centrifugal pressure investment-casting, vacuum pressure investment-casting, and powder casting, and wherein the curved piston and the curved cylinder have curved surfaces that mate with each other and are smoothened by a second precision manufacturing technique selected from the group consisting of flexible honing, electropolishing, and electroplating, wherein the curved piston and the curved cylinder are thereby formed with the mating curved surfaces sufficiently mating that they minimize binding and fluid leaking.*

* * * * *